(12) United States Patent
Horiuchi et al.

(10) Patent No.: US 12,268,468 B2
(45) Date of Patent: Apr. 8, 2025

(54) RADIOGRAPHY SYSTEM, METHOD FOR OPERATING RADIOGRAPHY SYSTEM, AND OPERATION PROGRAM FOR RADIOGRAPHY SYSTEM

(71) Applicant: FUJIFILM CORPORATION, Tokyo (JP)

(72) Inventors: Hisatsugu Horiuchi, Tokyo (JP); Yuji Jibiki, Tokyo (JP); Yuji Kai, Tokyo (JP); Koji Taninai, Tokyo (JP); Masataka Sugahara, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 152 days.

(21) Appl. No.: 18/170,531

(22) Filed: Feb. 17, 2023

(65) Prior Publication Data
US 2023/0270334 A1    Aug. 31, 2023

(30) Foreign Application Priority Data

Feb. 28, 2022 (JP) .................................. 2022-030382

(51) Int. Cl.
| | |
|---|---|
| *A61B 5/00* | (2006.01) |
| *A61B 5/107* | (2006.01) |
| *A61B 6/00* | (2006.01) |

(52) U.S. Cl.
CPC .......... *A61B 5/0064* (2013.01); *A61B 5/0077* (2013.01); *A61B 5/1071* (2013.01); *A61B 5/4566* (2013.01); *A61B 6/4464* (2013.01)

(58) Field of Classification Search
CPC ... A61B 5/0064; A61B 5/0077; A61B 5/1071; A61B 5/4566; A61B 5/4464
See application file for complete search history.

(56) References Cited

U.S. PATENT DOCUMENTS 5,762,608 A * 6/1998 Warne .................. A61B 6/4258
378/197
6,333,965 B1 * 12/2001 Van Berkel .............. H05G 1/36
378/98.7

(Continued)

FOREIGN PATENT DOCUMENTS

JP            6280676 B2    2/2018

OTHER PUBLICATIONS

Shu-Man et al. ; "Morphology and deformity of the shoulder and pelvis in the entire spine radiographs of adolescent idiopathic scoliosis"; Quantitative Imaging in Medicine and Surgery 2023;13(5):3266-3278 (Year: 2023).*

(Continued)

*Primary Examiner* — Dixomara Vargas
(74) *Attorney, Agent, or Firm* — SOLARIS Intellectual Property Group, PLLC

(57) ABSTRACT

A radiography system includes a radiation source that irradiates a subject with radiation, a camera, and a console. The camera is provided in the radiation source. The camera images the subject irradiated with illumination light that is, light having uniform brightness, to output an optical image. A CPU of the console has a first acquisition unit and a derivation unit. The first acquisition unit acquires the optical image from the camera. The derivation unit derives spinal column shape information representing a shape of a spinal column of the subject based on the optical image.

10 Claims, 24 Drawing Sheets

(56) References Cited

U.S. PATENT DOCUMENTS

| | | | | |
|---|---|---|---|---|
| 7,542,791 | B2* | 6/2009 | Mire | G16H 50/50 |
| | | | | 600/407 |
| 7,567,834 | B2* | 7/2009 | Clayton | A61B 5/06 |
| | | | | 600/427 |
| 2003/0215122 | A1* | 11/2003 | Tanaka | A61B 5/1075 |
| | | | | 382/128 |
| 2004/0240609 | A1* | 12/2004 | Spahn | A61B 6/488 |
| | | | | 378/63 |
| 2006/0120583 | A1* | 6/2006 | Dewaele | G06T 3/14 |
| | | | | 382/128 |
| 2007/0242869 | A1* | 10/2007 | Luo | G06T 7/0012 |
| | | | | 382/132 |
| 2015/0313566 | A1* | 11/2015 | Diers | A61B 6/505 |
| | | | | 378/63 |
| 2017/0119281 | A1* | 5/2017 | Herrmann | A61B 5/0013 |
| 2017/0119339 | A1* | 5/2017 | Johnson | A61B 6/58 |
| 2019/0057524 | A1* | 2/2019 | Kaltschmidt | G06T 11/005 |
| 2019/0320995 | A1* | 10/2019 | Amiri | A61B 6/4405 |
| 2020/0022758 | A1* | 1/2020 | Shoham | A61B 5/0077 |
| 2020/0069243 | A1* | 3/2020 | Matsumoto | A61B 5/0064 |
| 2021/0145519 | A1* | 5/2021 | Mosnier | G06N 3/04 |
| 2022/0414934 | A1* | 12/2022 | Aguzzi | G16H 50/20 |
| 2023/0127917 | A1* | 4/2023 | Kim | G06T 7/30 |
| | | | | 623/17.11 |
| 2023/0355309 | A1* | 11/2023 | Grupp, Jr. | A61B 17/8863 |
| 2024/0081761 | A1* | 3/2024 | Takahashi | A61B 5/4509 |
| 2024/0233246 | A1* | 7/2024 | El Hanchi El Amrani | |
| | | | | G06T 15/08 |

OTHER PUBLICATIONS

Ni et al.; "Spinal phantom comparability study of Cobb angle measurement of scoliosis using digital radiographic imaging"; Journal of Orthopaedic Translation vol. 15, Oct. 2018, pp. 81-90 (Year: 2018).*

David et al.; "Radiographic Evaluation of Scoliosis: Review"; AJR Integrative Imaging, Lifelong Learning for Radiology #194; (2010) pp. S8-S22 (Year: 2010).*

Kuklo et al.; "Correlation of radiographic, clinical, and patient assessment of shoulder balance following fusion versus nonfusion of the proximal Thoracic Curve in Adolescent Idiopathic Scoliosis"; Spine 27(18):p. 2013-2020, Sep. 15, 2002. (Year: 2002).*

* cited by examiner

RADIOGRAPHY SYSTEM, METHOD FOR OPERATING RADIOGRAPHY SYSTEM, AND OPERATION PROGRAM FOR RADIOGRAPHY SYSTEM

CROSS-REFERENCE TO RELATED APPLICATIONS

The present application claims priority under 35 U.S.C. § 119 to Japanese Patent Application No. 2022-030382, filed on Feb. 28, 2022. The above application is hereby expressly incorporated by reference, in its entirety, into the present application.

BACKGROUND

1. Technical Field

A technique of the present disclosure relates to a radiography system, a method for operating a radiography system, and an operation program for a radiography system.

2. Description of the Related Art

As part of medical care to scoliosis that a spinal column (spine, backbone) is curved right and left, a shape of a spinal column is ascertained from an optical image captured by a camera. The ascertainment of the shape of the spinal column based on the optical image is called a primary medical examination. The primary medical examination is performed before a secondary medical examination for ascertain the shape of the spinal column by a radiographic image showing the entire spinal column in more detail to determine a diagnosis of scoliosis. The primary medical examination is performed in a school medical examination based on School Health and Safety Act for the purpose of early detection of scoliosis.

JP6280676B describes a technique that derives spinal column shape information representing a shape of a spinal column of a subject using a moire fringe measurement apparatus. The moire fringe measurement apparatus comprises a light projection unit that irradiates the back of the subject with a light pattern for causing moire fringes, and a camera that images the back of the subject. Moire fringes representing a stereoscopic shape of the back of the subject are shown in the optical image captured by the camera. In JP6280676B, the spinal column shape information of the subject is derived by performing image analysis on the moire fringes shown in the optical image.

SUMMARY

Here, in a case where the ascertainment of the shape of the spinal column based on the optical image can be performed in conjunction with radiography of chest/upright/front that is substantially necessarily performed in a group medical examination, such as a school medical examination, the examination is performed in a short period of time as much, and burden on the subject is also reduced. As a quickest method for realizing the ascertainment of the shape of the spinal column based on the optical image in conjunction with radiography of chest/upright/front, a method in which the moire fringe measurement apparatus described in JP6280676B is provided in a radiation source that irradiates a subject with radiation is considered. Note that the moire fringe measurement apparatus described in JP6280676B has a large-scaled mechanism, such as the light projection unit that irradiates the back of the subject with the light pattern for causing moire fringes. For this reason, in a case where the moire fringe measurement apparatus described in JP6280676B is provided in the radiation source, another problem that handling of the radiation source is difficult occurs.

An embodiment according to the technique of the present disclosure provides a radiography system, a method for operating a radiography system, and an operation program for a radiography system capable of ascertaining a shape of a spinal column of a subject based on an optical image in conjunction with radiography without hindering the handling of a radiation source.

A radiography system of the present disclosure is a radiography system comprising a radiation source that irradiates a subject with radiation, a camera that is provided in the radiation source and images the subject irradiated with light having uniform brightness to output an optical image, and a processor, in which the processor is configured to acquire the optical image, and derive spinal column shape information representing a shape of a spinal column of the subject based on the optical image.

It is preferable that the processor is configured to extract a feature point of the subject from the optical image, extract derivation reference information for deriving the spinal column shape information from the feature point, and derive a polynomial representing the shape of the spinal column as the spinal column shape information based on the derivation reference information.

It is preferable that the processor is configured to calculate a Cobb angle indicating a degree of curvature of the spinal column from the polynomial. In this case, it is preferable that the processor is configured to perform control for displaying the Cobb angle on a display.

It is preferable that the processor is configured to determine whether or not a secondary medical examination of scoliosis by radiography is needed for the subject, based on the Cobb angle, and perform control for displaying a determination result on a display.

It is preferable that the processor is configured to extract right and left shoulder joint points, right and left hip joint points, points indicating a maximum width of right and left armpits of an upper body, and points indicating a minimum width of the right and left armpits of the upper body of the subject, as the feature point, and extract position coordinates of a middle point of a line connecting the right and left shoulder joint points, position coordinates of a middle point of a line connecting the right and left hip joint points, position coordinates of a middle point of a line connecting the points indicating the maximum width, and position coordinates of a middle point of a line connecting the points indicating the minimum width, as the derivation reference information.

It is preferable that the processor is configured to extract right and left shoulder joint points and right and left hip joint points of the subject, as the feature point, and extract position coordinates of a middle point of a line connecting the right and left shoulder joint points, position coordinates of a middle point of a line connecting the right and left hip joint points, an inclination of the line connecting the right and left shoulder joint points, and an inclination of the line connecting the right and left hip joint points, as the derivation reference information.

It is preferable that the processor is configured to, prior to the derivation of the spinal column shape information based on the optical image, acquire information regarding a body height of the subject, extract right and left shoulder joint points and right and left hip joint points of the subject, as the feature point, determine whether or not the derivation of the spinal column shape information based on the optical image is needed, based on the body height of the subject and a length of a line that connects a middle point of a line connecting the right and left shoulder joint points and a middle point of a line connecting the right and left hip joint points, and perform control for displaying a determination result on a display.

It is preferable that the processor is configured to perform control for displaying a past optical image acquired in a past on a display to be superimposed on a current optical image at the time of imaging preparation before the derivation of the spinal column shape information in a case of performing again the derivation of the spinal column shape information on the subject subjected to the derivation of the spinal column shape information based on the optical image in the past.

It is preferable that the radiation source is a ceiling suspension type.

A method for operating a radiography system of the present disclosure is a method for operating a radiography system including a radiation source that irradiates a subject with radiation, the method comprising acquiring an optical image output from a camera that is provided in the radiation source and images the subject irradiated with light having uniform brightness, and deriving spinal column shape information representing a shape of a spinal column of the subject based on the optical image.

An operation program for a radiography system of the present disclosure is an operation program for a radiography system including a radiation source that irradiates a subject with radiation, the operation program causing a computer to execute a process, the process comprising acquiring an optical image output from a camera that is provided in the radiation source and images the subject irradiated with light having uniform brightness, and deriving spinal column shape information representing a shape of a spinal column of the subject based on the optical image.

According to the technique of the present disclosure, it is possible to provide a radiography system, a method for operating a radiography system, and an operation program for a radiography system capable of ascertaining a shape of a spinal column of a subject based on an optical image in conjunction with radiography without hindering the handling of a radiation source.

BRIEF DESCRIPTION OF THE DRAWINGS

Exemplary embodiments according to the technique of the present disclosure will be described in detail based on the following figures, wherein:

FIG. 15A shows a case where both a first Cobb angle and a second Cobb angle are less than a first threshold value and FIG. 15B shows a case where any of the first Cobb angle and the second Cobb angle is equal to or greater than the first threshold value;

FIG. 20A shows a case where a ratio of a length of a line that connects a middle point of a line connecting right and left shoulder joint points and a middle point of a line connecting right and left hip joint points, to a body height is equal to or greater than a second threshold value and FIG. 20B shows a case where the ratio of a length of the line that connects the middle point of the line connecting the right and left shoulder joint points and the middle point of the line connecting the right and left hip joint points, to the body height is less than the second threshold value;

DETAILED DESCRIPTION

First Embodiment

Figure 1:
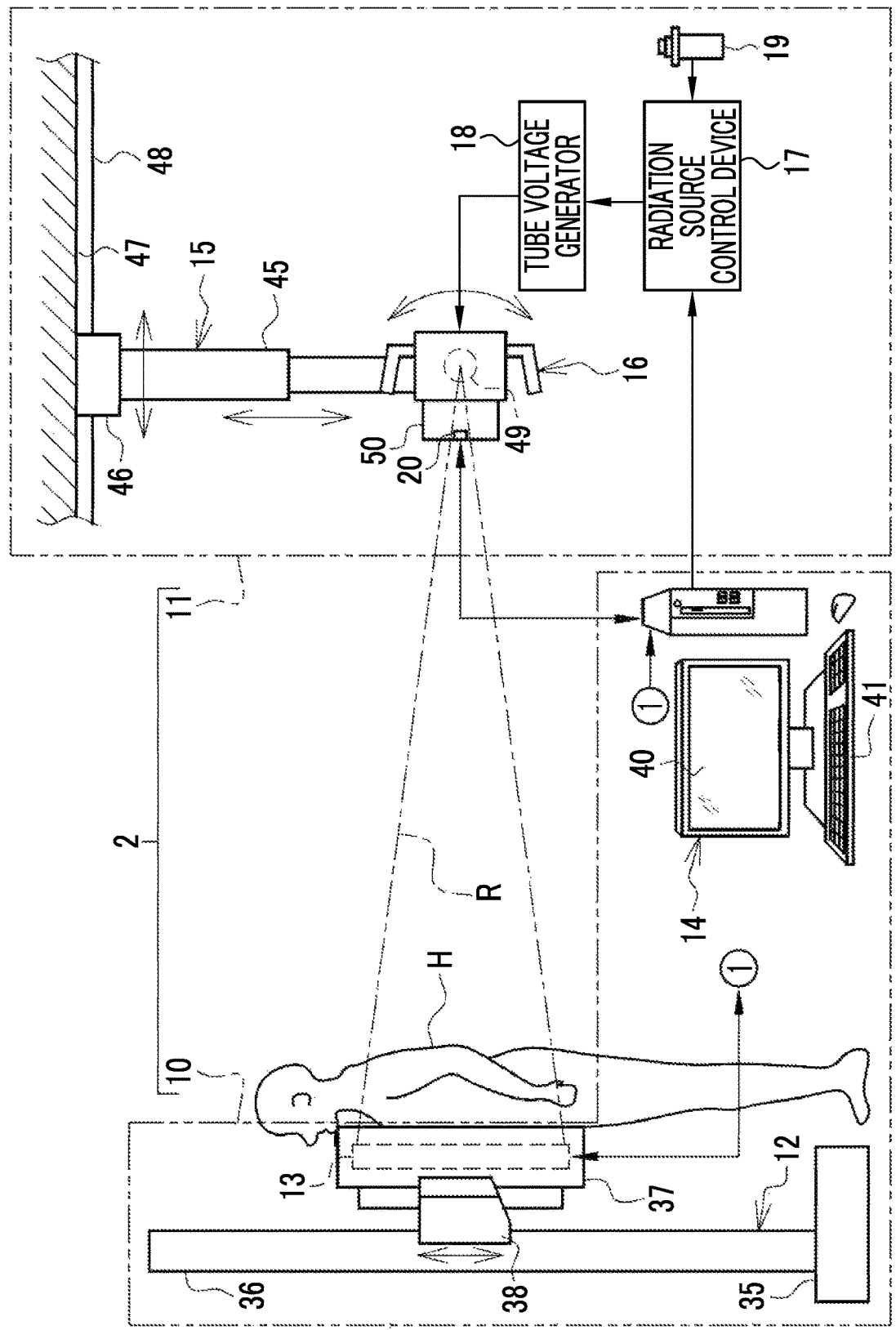
FIG. 1 is a diagram showing a radiography system.

As shown in FIG. 1 as an example, a radiography system 2 is a system that performs radiography of a subject H using radiation R, such as X-rays or y-rays, and is configured with a radiography apparatus 10 and a radiation generation apparatus 11. The radiography apparatus 10 has an upright imaging stand 12, an electronic cassette 13, and a console 14. The radiation generation apparatus 11 has a radiation source suspension device 15, a radiation source 16, a radiation source control device 17, a tube voltage generator 18, and an irradiation switch 19. A camera 20 is attached to the radiation source 16.

Figure 2:
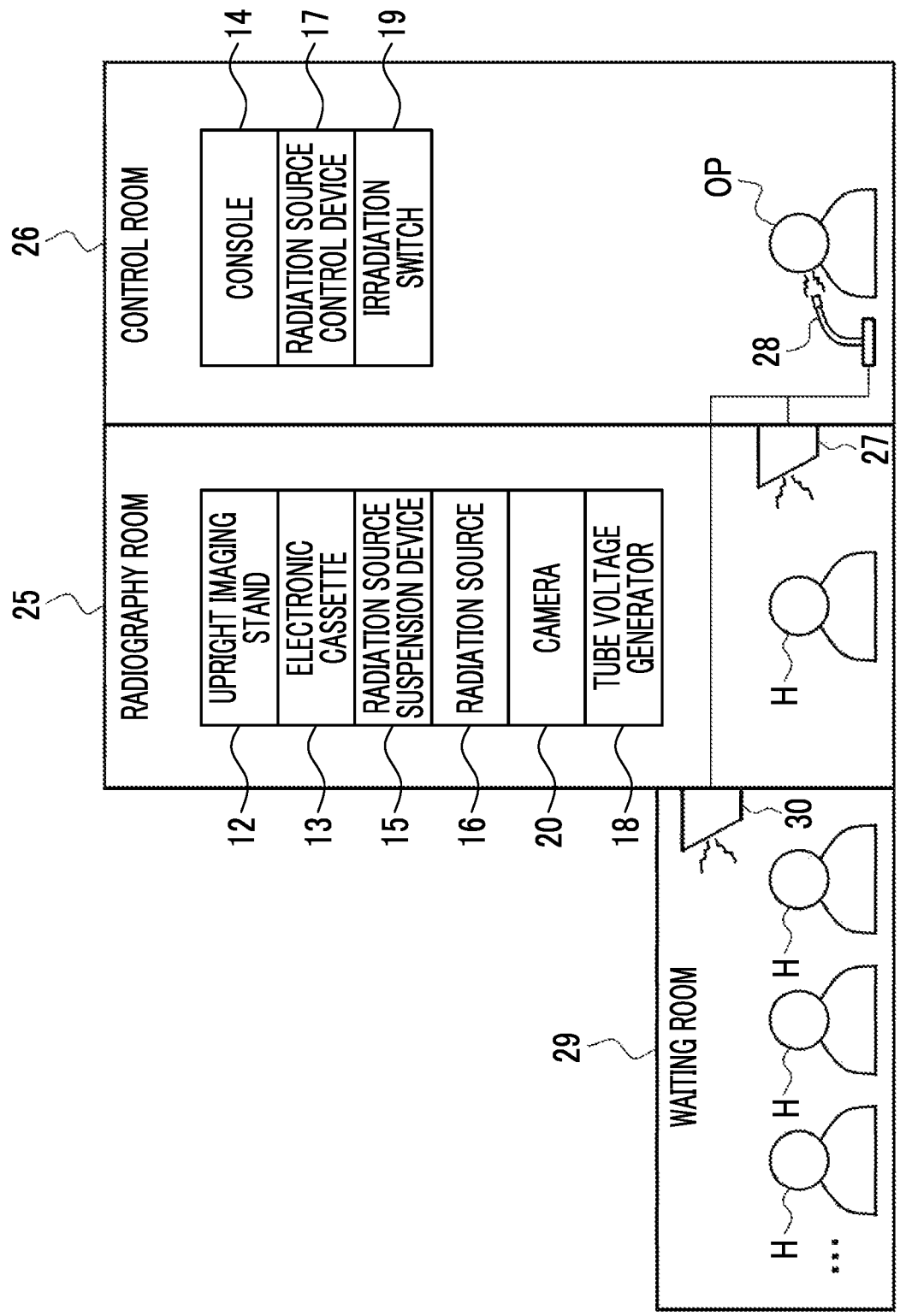
FIG. 2 is a diagram showing a radiography room, a control room, and a waiting room.

As shown in FIG. 2 as an example, the upright imaging stand 12, the electronic cassette 13, the radiation source suspension device 15, the radiation source 16, the camera 20, and the tube voltage generator 18 are provided in a radiography room 25. On the other hand, the console 14, the radiation source control device 17, and the irradiation switch 19 are provided in a control room 26 next to the radiography room 25. A speaker 27 is provided in the radiography room 25, and a microphone 28 is provided in the control room 26. The speaker 27 outputs spoken voice of an operator OP, such as a radiographer, in the control room 26, collected by the microphone 28. It is possible to achieve communication between the subject H in the radiography room 25 and the operator OP in the control room 26 by the speaker 27 and the microphone 28. A speaker 30 is provided in a waiting room 29 of the subject H. Through the speaker 30 and the microphone 28, the operator OP performs announcement for guiding the subject H having the turn of radiography from the waiting room 29 to the radiography room 25.

The subject H is, for example, a medical examinee of a group medical examination, such as a school medical examination. In this case, as radiography, chest/upright/front imaging illustrated in FIG. 1 is performed on each subject H.

Returning to FIG. 1, the upright imaging stand 12 is an imaging stand for radiographing the subject H in an upright posture. The upright imaging stand 12 has a pedestal 35 that is provided on a floor surface of the radiography room 25, a support 36 that extends in a height direction from the pedestal 35, and a holder 37 that holds the electronic cassette 13 inside. The holder 37 is connected to the support 36 through a connection portion 38. The connection portion 38 and the holder 37 are moved up and down with respect to the support 36 by a motor or the like conforming to an imaging part or the physique of the subject H. A position where the holder 37 is moved up and down with respect to the support 36 is detected by, for example, a linear encoder. The moving up and down of the holder 37 can be performed from the control room 26 through the console 14.

The electronic cassette 13 is a portable radiographic image detector that detects a radiographic image 66 (see FIG. 4) depending on the radiation R transmitted through the subject H. The electronic cassette 13 is connected to the console 14 to be communicable in a wired or wireless manner. The electronic cassette 13 is accommodated in the holder 37 of the upright imaging stand 12 for use. The electronic cassette 13 may be detached from the holder 37 and carried by the subject H or may be inserted below the subject H who lies supine on a bed of a patient's room for use.

The electronic cassette 13 has a detection panel in which a plurality of pixels for accumulating electric charge depending on the radiation R are arranged in a two-dimensional matrix. The detection panel is also called a flat panel detector (FPD). In a case where the irradiation of the radiation R is started, the detection panel starts an accumulation operation to accumulate the electric charge in the pixels. In a case where the irradiation of the radiation R is ended, the detection panel starts a readout operation to read out the electric charge accumulated in the pixels as an electrical signal.

The console 14 is, for example, a desktop type personal computer. The console 14 has a display 40 that displays various screens, and an input device 41 that includes a keyboard, a mouse, and the like and receives an operation instruction of the operator OP. The console 14 transmits various signals to the electronic cassette 13. The console 14 receives the radiographic image 66 from the electronic cassette 13. The console 14 displays the radiographic image 66 on the display 40. The display 40 is an example of a "display" according to the technique of the present disclosure. The console 14 may be a notebook type personal computer, a tablet terminal, or the like.

The radiation source suspension device 15 has an arm 45 and a carriage 46. The radiation source 16 is attached to a distal end of the arm 45, and a proximal end of the arm 45 is attached to the carriage 46. The arm 45 can expand and contract along a vertical direction by a motor or the like. The arm 45 is made to expand and contract in the vertical direction, so that a height position of the radiation source 16 can be changed conforming to the imaging part or the physique of the subject H. A position of expansion and contraction of the arm 45 and the height position of the radiation source 16 are detected by, for example, a linear encoder. The radiation source 16 is rotated around an axis perpendicular to the paper plane with respect to the arm 45 by a motor or the like to adjust an incidence angle of the radiation R on the subject H. A rotation angle of the radiation source 16 is detected by, for example, a rotary encoder or a potentiometer. Like the moving up and down of the holder 37, the moving up and down and the rotation of the radiation source 16 can also be performed from the control room 26 through the console 14.

The carriage 46 is connected to a rail 48 provided on a ceiling 47 of the radiography room 25. That is, the radiation source 16 is a ceiling suspension type. The rail 48 has a linear shape and is parallel to a normal line of a detection surface for the radiation R of the electronic cassette 13 accommodated in the holder 37. The carriage 46 and the radiation source 16 can be moved in parallel along the rail 48 by a motor or the like. The radiation source 16 is moved in parallel along the rail 48 in this manner, so that a source to image receptor distance (SID) that is a distance from a generation point of the radiation R to the detection surface for the radiation R of the electronic cassette 13 is changed. A position of the carriage 46 with respect to the rail 48 is detected by, for example, a linear encoder. Like the moving up and down of the holder 37, the parallel movement of the radiation source 16 can also be performed from the control room 26 through the console 14.

The radiation source 16 has a radiation tube 49 and an irradiation field limiter 50. The radiation tube 49 is provided with a filament, a target, a grid electrode, and the like (all are not shown). A voltage is applied between the filament as a cathode and the target as an anode. The voltage that is applied between the filament and the target is referred to as a tube voltage. The filament discharges thermoelectrons depending on the applied tube voltage toward the target. The target radiates the radiation R with collision of the thermoelectrons from the filament. The grid electrode is disposed between the filament and the target. The grid electrode changes a flow rate of the thermoelectrons from the filament toward the target depending on the applied voltage. The flow rate of the thermoelectrons from the filament toward the target is referred to as a tube current.

The irradiation field limiter 50 is also called a collimator and limits an irradiation field of the radiation R emitted from the radiation tube 49. The irradiation field limiter 50 has, for example, a configuration in which four shield plates formed of lead or the like that shield the radiation R are disposed on respective sides of a quadrangle, and a quadrangular emission opening through which the radiation R is transmitted is formed in a center portion. The irradiation field limiter 50 changes a position of each shield plate to change the size of the emission opening, and accordingly, changes the irradiation field of the radiation R.

The tube voltage generator 18 and the irradiation switch 19 are connected to the radiation source control device 17. The radiation source control device 17 controls the operation of the radiation source 16 in response to various command signals from the irradiation switch 19. The irradiation switch 19 is operated in a case where the operator OP instructs the radiation source 16 to start the irradiation of the radiation R.

An irradiation condition 63 (see FIG. 4) of the radiation R is set in the radiation source control device 17. The irradiation condition 63 is a tube voltage that is applied to the radiation tube 49, a tube current, and an irradiation time of the radiation R (see FIG. 4). In a case where an instruction to start the irradiation of the radiation R is issued by the operation of the irradiation switch 19, the radiation source control device 17 operates the tube voltage generator 18 following the set irradiation condition 63, and causes the irradiation of the radiation R from the radiation tube 49. After the irradiation of the radiation R is started, in a case where the irradiation time set in the irradiation condition 63 has elapsed, the radiation source control device 17 stops the irradiation of the radiation R from the radiation tube 49. The tube voltage generator 18 boosts an input voltage by a transformer to generate the tube voltage. The tube voltage generated by the tube voltage generator 18 is supplied to the radiation tube 49 through a voltage cable (not shown).

The irradiation of the radiation R may be ended by an auto exposure control (AEC) function. The AEC function is a function of detecting a dose of the radiation R during the irradiation of the radiation R and stopping the irradiation of the radiation R from the radiation tube 49 at a point of time at which a cumulative dose that is an integrated value of the detected dose reaches a target dose set in advance. In this case, the detection panel of the electronic cassette 13 starts the readout operation in a case where the cumulative dose of the radiation R reaches the target dose.

Figure 3:
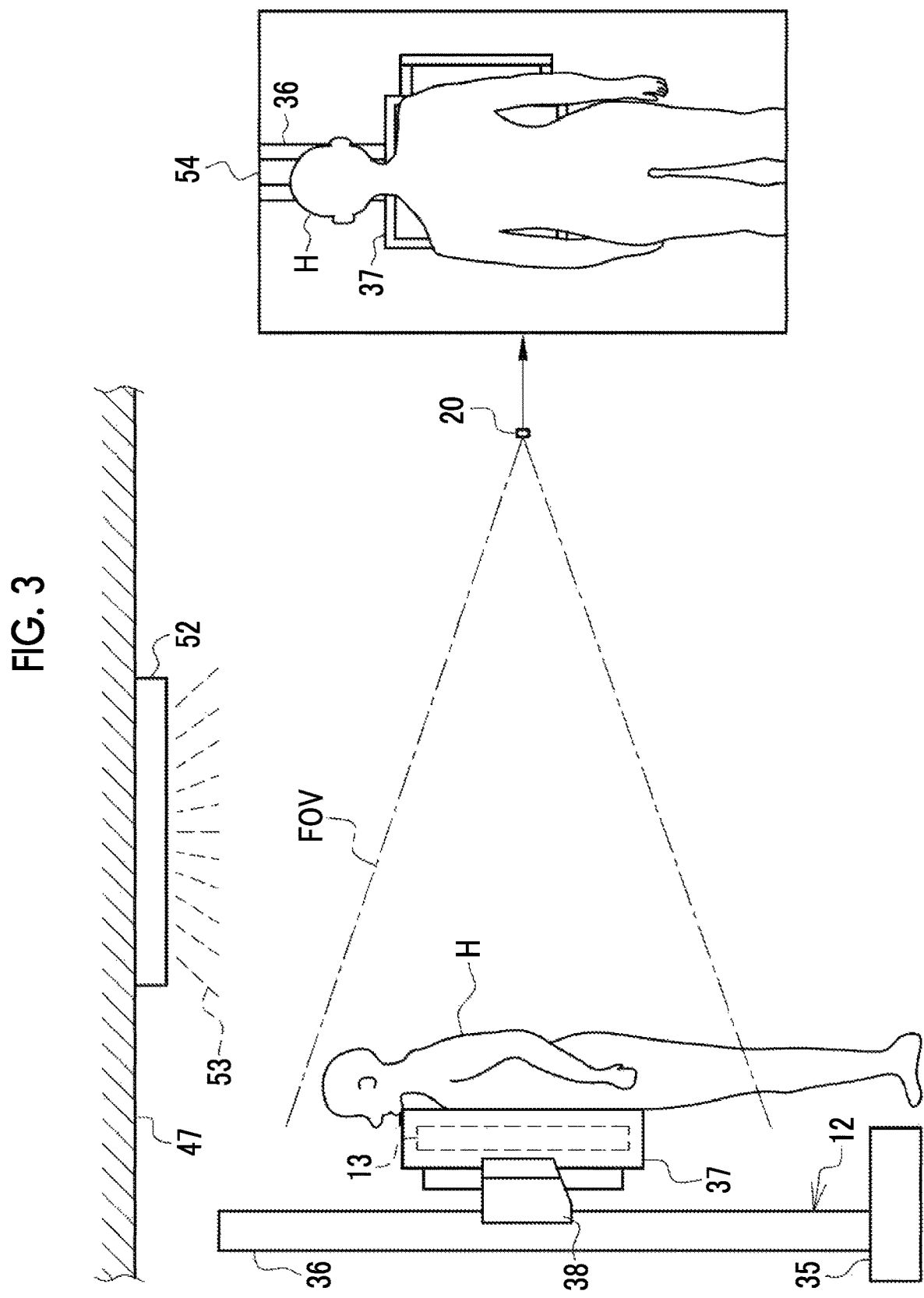
FIG. 3 is a diagram showing a manner in which an optical image is captured with a camera.

The camera 20 is a digital camera that captures a digital optical image 54 (see FIG. 3). The camera 20 is attached to the center of a distal end of the irradiation field limiter 50 of the radiation source 16. The camera 20 is connected to the console 14 to be communicable in a wired or wireless manner. The camera 20 images the subject H who stands before the upright imaging stand 12 for radiography, in response to an imaging instruction from the console 14. The imaging instruction of the optical image 54 to the camera 20 through the console 14 is performed by the operator OP, for example, after the subject H is guided from the waiting room 29 to the radiography room 25 and the subject H is made to stand before the upright imaging stand 12. The camera 20 transmits the captured optical image 54 to the console 14. The camera 20 may be incorporated in the irradiation field limiter 50.

FIG. 3 shows an example of a manner in which the subject H who stands before the upright imaging stand 12 is imaged with the camera 20 in response to the imaging instruction of the operator. The subject H is irradiated with illumination light 53 from a light source 52 provided on the ceiling 47 of the radiography room 25. The light source 52 is a white light source, such as a fluorescent light or a white light emitting diode (LED), and the illumination light 53 is white light. White light is light in which light (light having wavelength of 360 nm to 830 nm) having a wavelength of visible rays is substantially evenly mixed. The illumination light 53 is an example of "light having uniform brightness" according to the technique of the present disclosure. "Light having uniform brightness" refers to light in which a difference in brightness depending on a place falls within a specified range in a macroscopic space, such as the radiography room 25. "Light having uniform brightness" may be natural light (sunlight).

The camera 20 has a field of view (FOV) with which a portion from a head to below a knee (the whole of an upper body and a part of a lower body) of the back of the subject H who stands before the upright imaging stand 12 can be imaged. In the optical image 54 captured with the camera 20 in this manner, a part of the upright imaging stand 12 and the portion from the head to below the knee of the back of the subject H who stands before the upright imaging stand 12 are shown.

Figure 4:
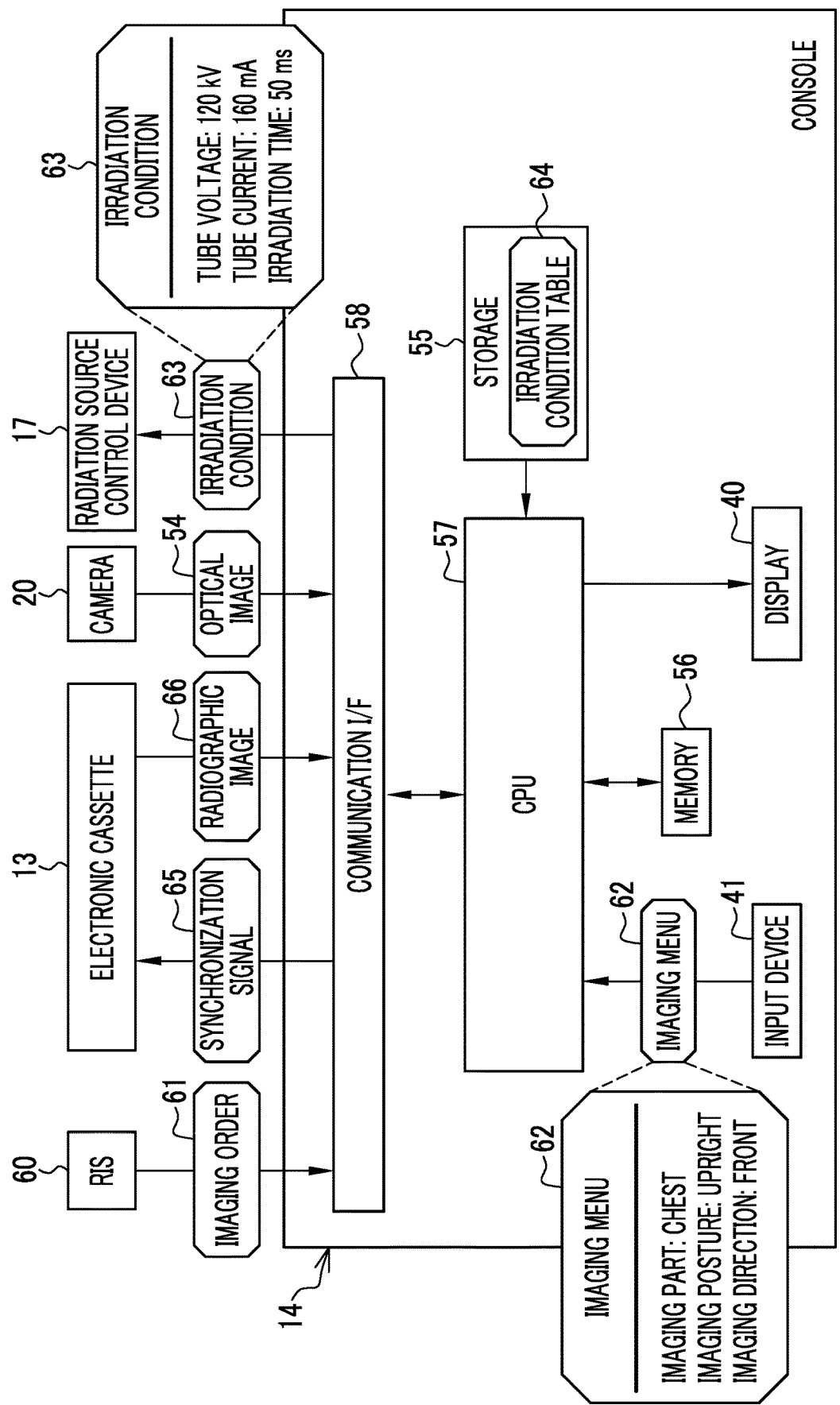
FIG. 4 is a block diagram showing the configuration of a console.

As shown in FIG. 4 as an example, the console 14 comprises a storage 55, a memory 56, a central processing unit (CPU) 57, and a communication interface (I/F) 58, in addition to the display 40 and the input device 41. The display 40, the input device 41, the storage 55, the memory 56, the CPU 57, and the communication I/F 58 are connected to one another through a bus line (not shown). The storage 55, the memory 56, the CPU 57, and the bus line are an example of a "computer" according to the technique of the present disclosure.

The storage 55 is a hard disk drive that is incorporated in a computer configuring the console 14 or is connected to the computer through a cable or a network. In the storage 55, a control program, such as an operating system, various application programs, various kinds of data associated with such programs, and the like are stored. A solid state drive may be used instead of the hard disk drive.

The memory 56 is a work memory on which the CPU 57 executes processing. The CPU 57 loads the programs stored in the storage 55 to the memory 56 to execute processing depending on the programs. With this, the CPU 57 integrally controls each unit of the computer. The CPU 57 is an example of a "processor" according to the technique of the present disclosure. The memory 56 may be incorporated in the CPU 57. The communication I/F 58 performs transmission control of various kinds of information with an external apparatus, such as the electronic cassette 13.

The CPU 57 receives an imaging order 61 from a radiology information system (RIS) 60 through the communication I/F 58. In the imaging order 61, subject identification data (ID) 161 (see FIG. 23) for identifying the subject H, an instruction of an imaging procedure by a treatment department physician or the like who issues the imaging order 61, and the like are registered. The CPU 57 displays the imaging order 61 on the display 40 depending on an operation of the operator OP by the input device 41. The operator OP confirms the contents of the imaging order 61 through the display 40.

The CPU 57 displays a plurality of kinds of imaging menus 62 on the display 40 in a selectable form. The imaging menu 62 specifies an imaging procedure having a set of an imaging part of the subject H, an imaging posture of the subject H, and an imaging direction of the subject H, such as "chest/upright/front". The imaging part is a head, a neck, an abdomen, a waist, a shoulder, an elbow, a hand, a knee, an ankle, and the like, in addition to the chest. The imaging posture includes a decubitus posture, a sitting posture, and the like, in addition to the upright posture. The imaging direction is a rear surface, a lateral surface, and the like, in addition to the front surface. The operator OP operates the input device 41 to select one imaging menu 62 matching the imaging procedure designated in the imaging order 61 among a plurality of kinds of imaging menus 62. With this, the CPU 57 receives the imaging menu 62. The CPU 57 reads out an irradiation condition 63 corresponding to the received imaging menu 62 from an irradiation condition table 64 stored in the storage 55. The CPU 57 displays the read-out irradiation condition 63 on the display 40. In the irradiation condition table 64, the irradiation conditions 63 corresponding to various imaging menus 62 are registered. The irradiation condition 63 is the tube voltage that is applied to the radiation tube 49, the tube current, and the irradiation time of the radiation R as described above. Instead of the tube current and the irradiation time, a tube current and irradiation time product may be set as the irradiation condition 63.

The CPU 57 transmits the set irradiation condition 63 to the radiation source control device 17 through the communication I/F 58. Though not shown, in a case where the instruction to start the irradiation of the radiation R is issued to the radiation source control device 17 through the irradiation switch 19, the CPU 57 receives an irradiation start signal indicating that the irradiation of the radiation R is started, from the radiation source control device 17. In a case where the irradiation start signal is received, the CPU 57 transmits a synchronization signal 65 indicating that the irradiation of the radiation R is started, to the electronic cassette 13. The CPU 57 receives an irradiation end signal indicating that the irradiation of the radiation R ends, from the radiation source control device 17. In a case where the irradiation end signal is received, the CPU 57 transmits a synchronization signal 65 indicating that the irradiation of the radiation R ends, to the electronic cassette 13.

In a case where the synchronization signal 65 indicating that the irradiation of the radiation R is started is received from the console 14, the electronic cassette 13 makes the detection panel start the accumulation operation. In a case where the synchronization signal 65 indicating that the irradiation of the radiation R ends is received from the console 14, the electronic cassette 13 makes the detection panel start the readout operation. A function of detecting the irradiation start and the irradiation end of the radiation R may be provided in the electronic cassette 13, in a case where the irradiation start of the radiation R is detected by the function, the detection panel may be made to start the accumulation operation, and in a case where the irradiation end of the radiation R is detected, the detection panel may be made to start the readout operation.

The CPU 57 receives the radiographic image 66 from the electronic cassette 13 through the communication I/F 58. The CPU 57 executes various kinds of image processing on the radiographic image 66, then, displays the radiographic image 66 on the display 40, and allows the operator to browse the radiographic image 66.

Though not shown, the CPU 57 transmits the imaging instruction to the camera 20 through the communication I/F 58. The CPU 57 receives the optical image 54 captured by the camera 20 in response to the imaging instruction.

Figure 5:
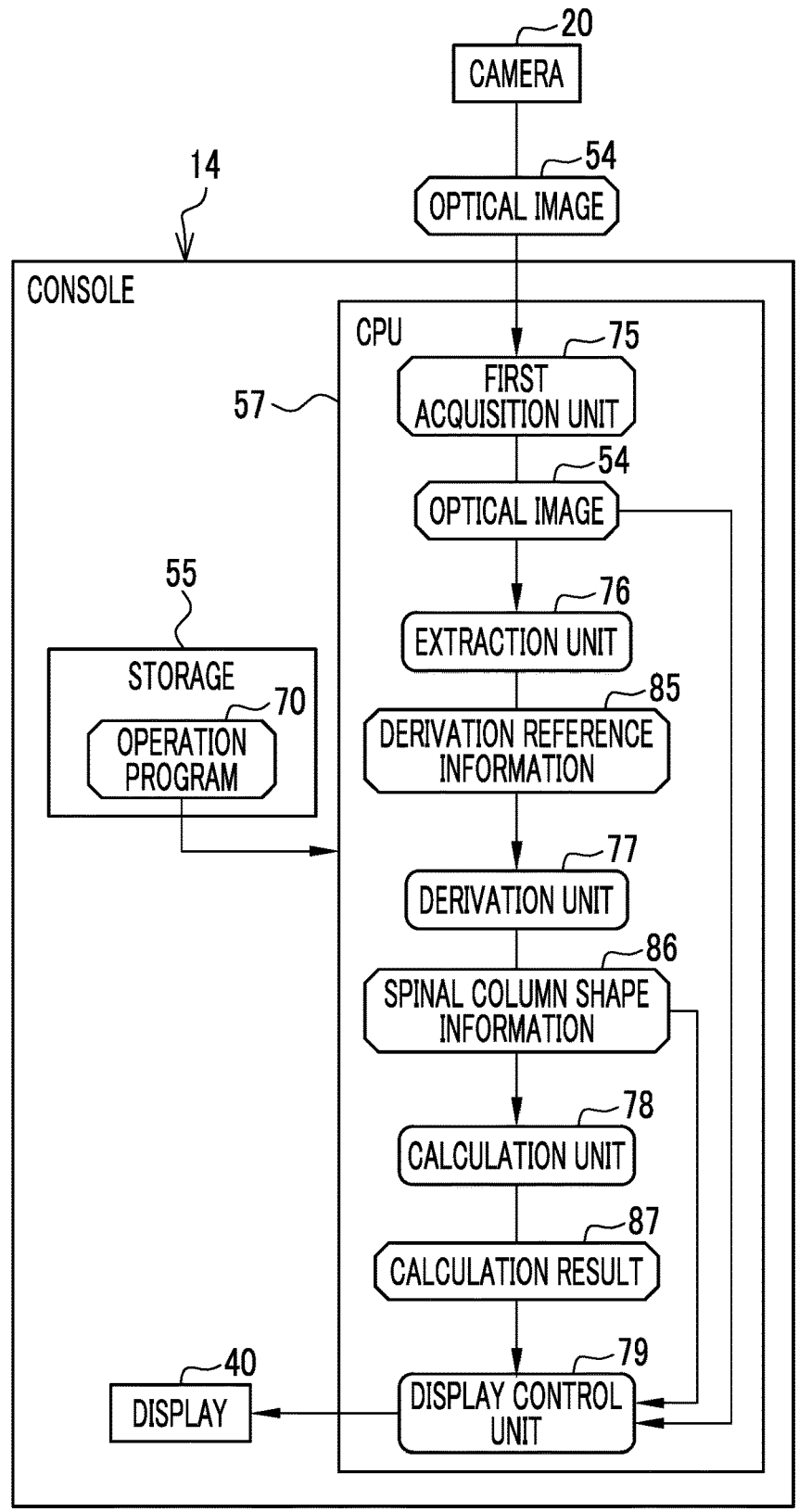
FIG. 5 is a block diagram showing processing units of a CPU of the console.

As shown in FIG. 5 as an example, an operation program 70 is stored in the storage 55. The operation program 70 is an example of an "operation program for a radiography system" according to the technique of the present disclosure.

In a case where the operation program 70 is started, the CPU 57 functions as a first acquisition unit 75, an extraction unit 76, a derivation unit 77, a calculation unit 78, and a display control unit 79 in cooperation with the memory 56 and the like.

The first acquisition unit 75 sequentially acquires the optical images 54 output from the camera 20 at a predetermined frame rate. The first acquisition unit 75 outputs the optical image 54 to the extraction unit 76 and the display control unit 79.

The extraction unit 76 executes image processing on the optical image 54 and extracts derivation reference information 85 for deriving spinal column shape information 86 representing a shape of a spinal column of the subject H. The extraction unit 76 outputs the derivation reference information 85 to the derivation unit 77.

The derivation unit 77 derives the spinal column shape information 86 based on the derivation reference information 85. The derivation unit 77 outputs the spinal column shape information 86 to the calculation unit 78 and the display control unit 79.

The calculation unit 78 calculates a Cobb angle indicating a degree of curvature of the spinal column of the subject H from the spinal column shape information 86. The calculation unit 78 outputs a calculation result 87 of the Cobb angle to the display control unit 79.

The display control unit 79 performs control for displaying various screens on the display 40. Various screens include a display screen of the imaging order 61, a selection screen of the imaging menu 62, an information display screen 100 (see FIG. 10), and the like. Though not shown, the CPU 57, in addition to the processing units 75 to 79, a reception unit 160 (see FIG. 23) that receives the imaging order 61 from the RIS 60, an image processing unit that executes various kinds of image processing on the radiographic image 66, a setting unit that sets the irradiation condition 63 in the radiation source control device 17, and the like are constructed.

Figure 6:
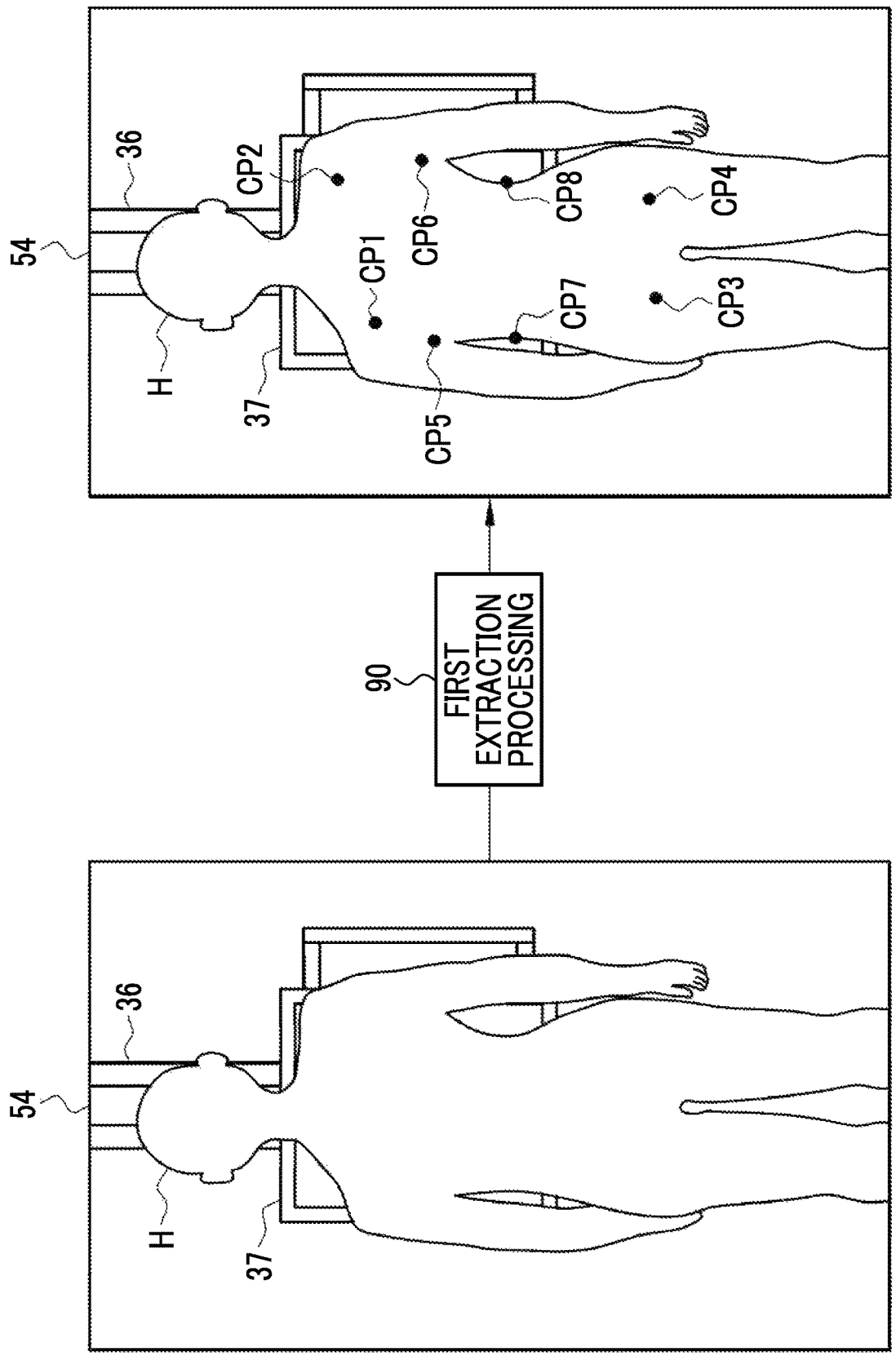
FIG. 6 is a diagram showing processing of an extraction unit.

As shown in FIG. 6 as an example, the extraction unit 76 executes first extraction processing 90 on the optical image 54. The first extraction processing 90 is processing of extracting feature points of the subject H shown in the optical image 54 using a known image recognition technique or a machine learning model. The feature points are right and left shoulder joint points CP1 and CP2, right and left hip joint points CP3 and CP4, points CP5 and CP6 indicating a maximum width of right and left armpits of an upper body, and points CP7 and CP8 indicating a minimum width of the right and left armpits of the upper body. The shoulder joint points are connection points of shoulder bones and upper arm bones. The hip joint points are connection points of coxal bones and a thighbone. The points indicating the maximum width are points below the armpits, and are, for example, points through which a measure passes in measuring a circumference of a chest. The points indicating the minimum width are points at constricted positions of a waist, and are, for example, points through which a measure passes in measuring a circumference of an abdomen.

Figure 7:
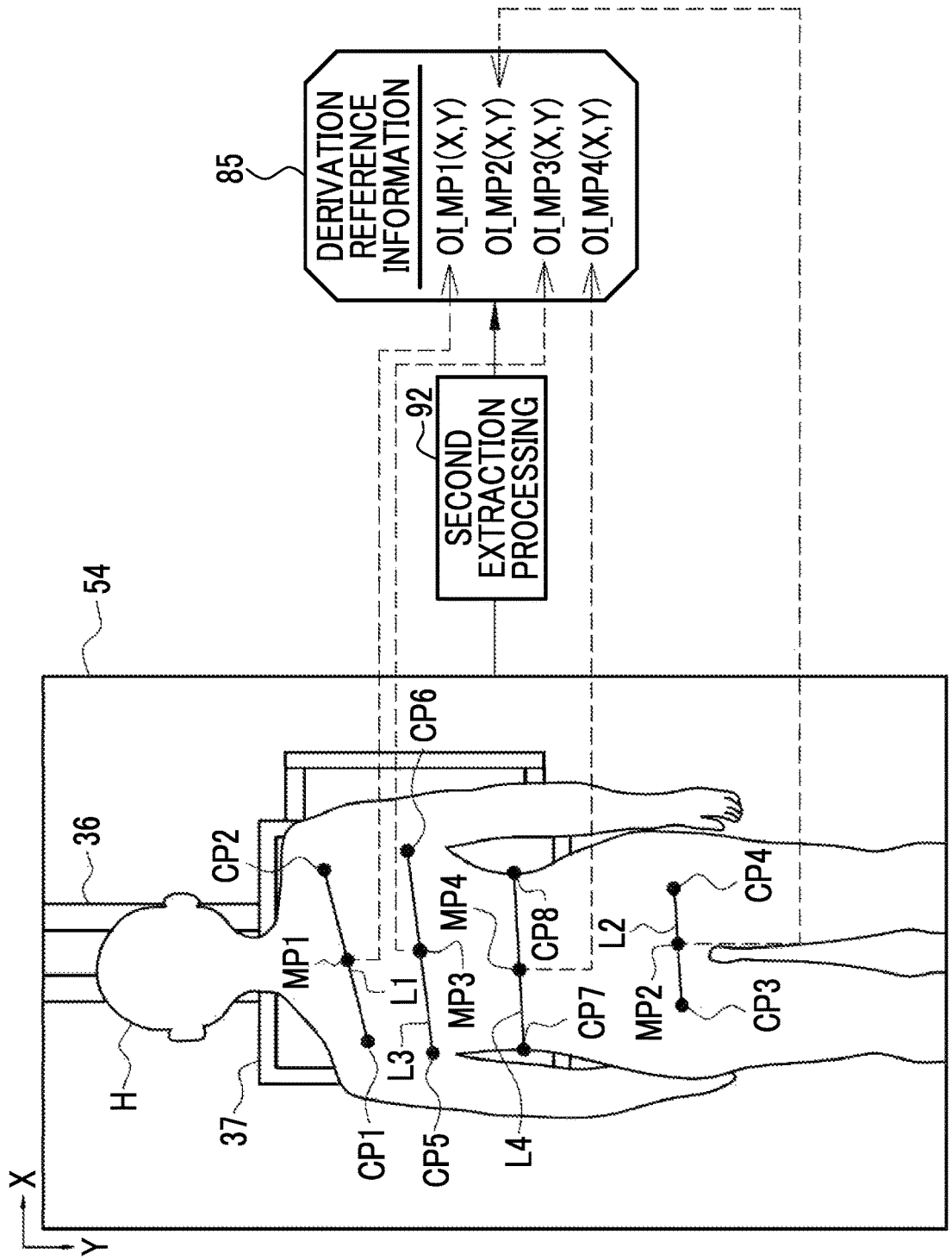
FIG. 7 is a diagram showing processing of the extraction unit.

As shown in FIG. 7 as an example, the extraction unit 76 executes second extraction processing 92 on the optical image 54 after the first extraction processing 90. The second extraction processing 92 is processing of extracting position coordinates OI_MP1(X,Y) of a middle point MP1 of a line L1 connecting the right and left shoulder joint points CP1 and CP2, position coordinates OI_MP2(X,Y) of a middle point MP2 of a line L2 connecting the right and left hip joint points CP3 and CP4, position coordinates OI_MP3(X,Y) of a middle point MP3 of a line L3 connecting the points CP5 and CP6 indicating the maximum width, and position coordinates OI_MP4(X,Y) of a middle point MP4 of a line L4 connecting the points CP7 and CP8 indicating the minimum width, as the derivation reference information 85. An origin of position coordinates OI(X,Y) of the optical image 54 is a left end of the optical image 54, the X axis is a direction along a short side of the optical image 54, and the Y axis is a direction along a long side of the optical image 54.

Figure 8:
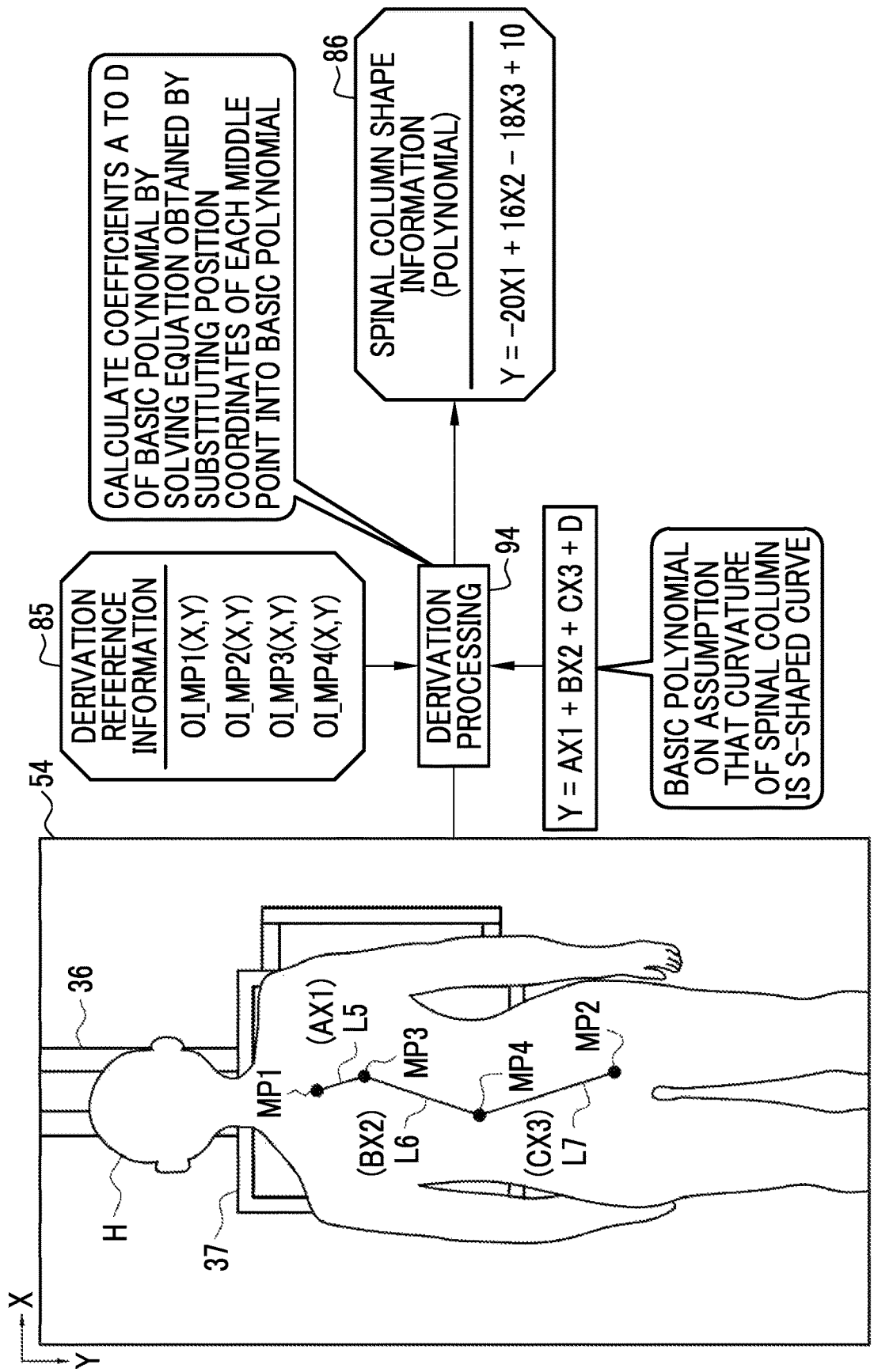
FIG. 8 is a diagram showing processing of a derivation unit.

As shown in FIG. 8 as an example, the derivation unit 77 executes derivation processing 94 on the optical image 54. The derivation processing 94 is processing of calculating coefficients A to D of a basic polynomial by solving an equation obtained by substituting the position coordinates OI_MP1(X,Y) to OI_MP4(X,Y) of the respective middle points MP1 to MP4 of the derivation reference information 85 into a basic polynomial $Y=AX1+BX2+CX3+D$ as a cubic polynomial on an assumption that a curvature of the spinal column is an S-shaped curve. A first term AX1 of the basic polynomial is a line L5 that connects the middle point MP 1 of the line L1 connecting the right and left shoulder joint points CP1 and CP2 and the middle point MP3 of the line L3 connecting the points CP5 and CP6 indicating the maximum width, and A is an inclination of the line L5. A second term BX2 is a line L6 that connects the middle point MP3 of the line L3 connecting the points CP5 and CP6 indicating the maximum width, the middle point MP4 of the line L4 connecting the points CP7 and CP8 indicating the minimum width, and B is an inclination of the line L6. Similarly, a third term CX3 is a line L7 that connects the middle point MP4 of the line L4 connecting the points CP7 and CP8 indicating the minimum width and the middle point MP2 of the line L2 connecting the right and left hip joint points CP3 and CP4, and C is an inclination of the line L7. D is a section in which respective sections of the lines L5 to L7 are combined.

The derivation unit 77 derives a polynomial representing the shape of the spinal column of the subject H, as the spinal column shape information 86 through the derivation processing 94. In FIG. 8, a case where $A=-20$, $B=16$, $C=-18$, and $D=10$, and the polynomial is $Y=-20X1+16X2-18X3+10$ is illustrated.

Figure 9:
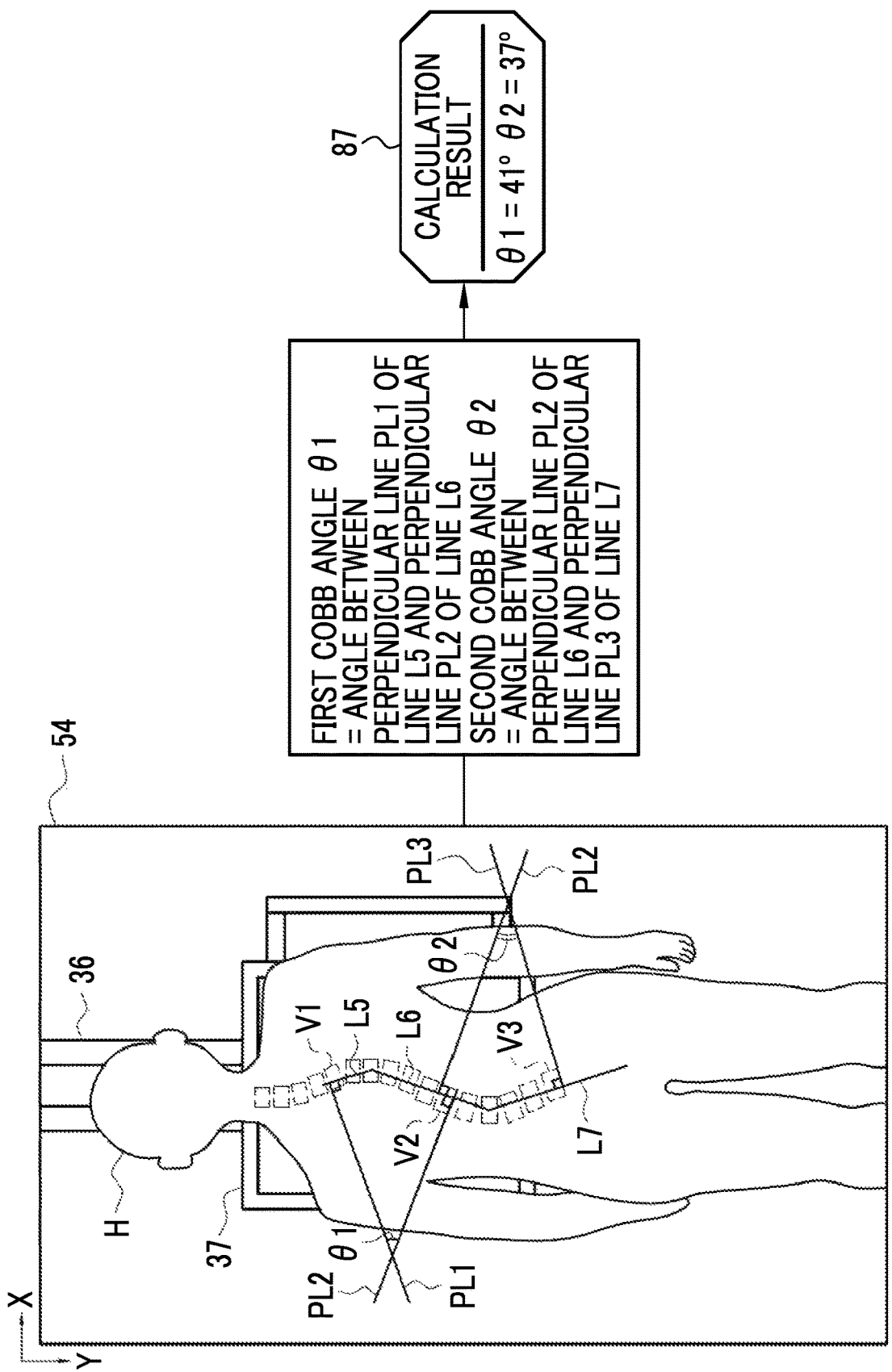
FIG. 9 is a diagram showing processing of a calculation unit.

As shown in FIG. 9 as an example, the calculation unit 78 calculates a Cobb angle from a polynomial. In more detail, the calculation unit 78 calculates an angle between a perpendicular line PL1 of the line L5 and a perpendicular line PL2 of the line L6, as a first Cobb angle $\theta 1$. The calculation unit 78 calculates an angle between the perpendicular line PL2 of the line L6 and a perpendicular line PL3 of the line L7, as a second Cobb angle $\theta 2$. The perpendicular line PL1 is a line parallel to an upper edge of a vertebral body V1 having a greatest inclination on a head side. The perpendicular line PL2 is a line parallel to an upper edge and a lower edge of a vertebral body V2 having a greatest inclination among vertebral bodies inclined in a direction opposite to the vertebral body V1 on a waist side. The perpendicular line PL3 is a line parallel to a lower edge of a vertebral body V3 having a greatest inclination among the vertebral bodies inclined in the direction opposite to the vertebral body V2 on the waist side. In FIG. 9, a case where 41° is calculated as the first Cobb angle $\theta 1$ and 37° is calculated as the second Cobb angle $\theta 2$ is illustrated.

Figure 10:
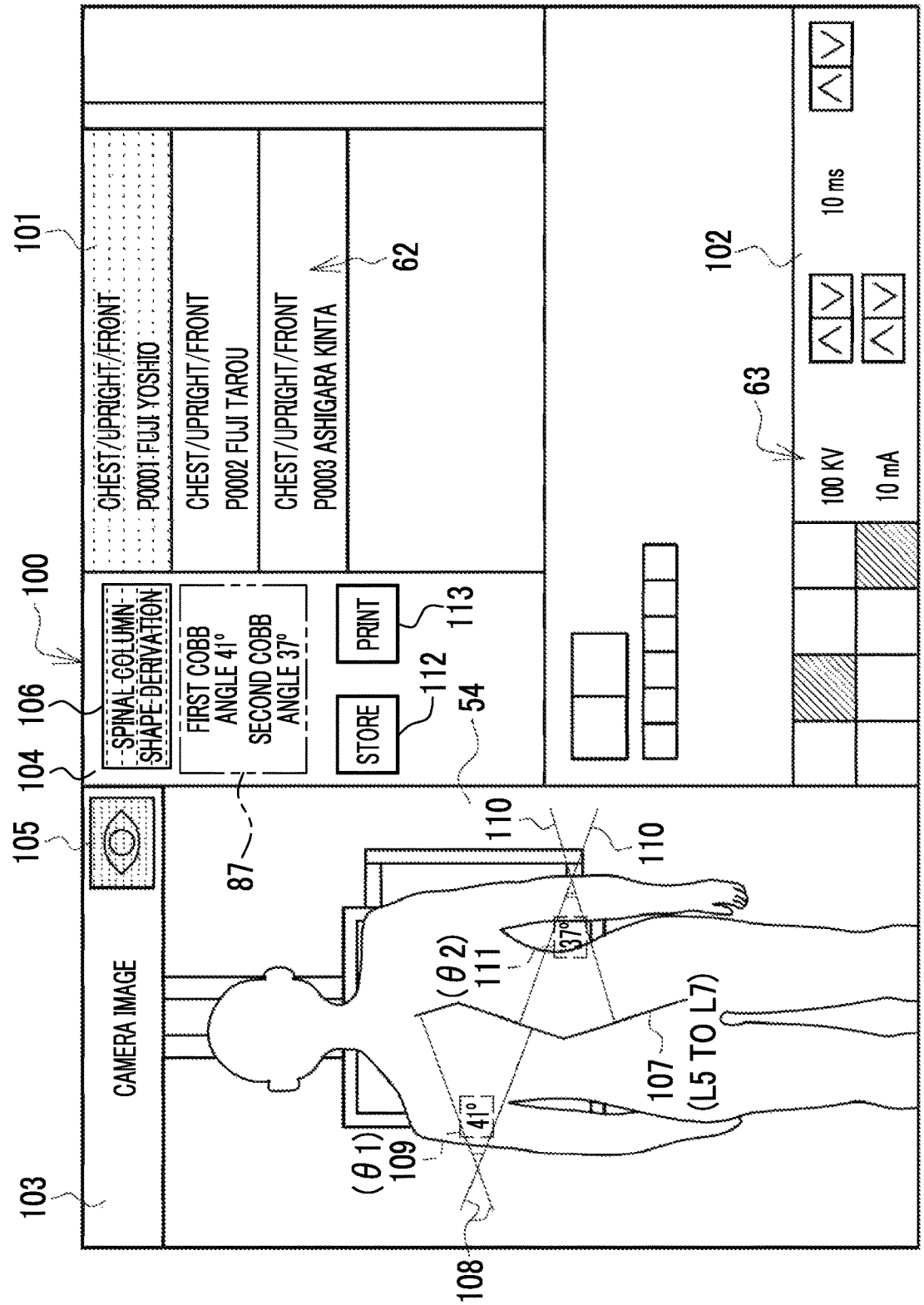
FIG. 10 is a diagram showing an information display screen.

As shown in FIG. 10 as an example, the information display screen 100 has a display region 101 of the imaging menu 62 and a display region 102 of the irradiation condition 63. In the display region 101, sets of the imaging menu 62, the subject ID 161 (P0001, P0002, or the like) and a name of the subject H registered so far are displayed in parallel. The imaging menu 62 with which radiography is currently performed is displayed in a color different from other imaging menus 62 as indicated by hatching. In the display region 102, the tube voltage, the tube current, and the irradiation time of the irradiation condition 63 are displayed in an adjustable state.

The information display screen 100 also has a display region 103 of the optical image 54 and a display region 104 of the calculation result 87. An imaging instruction button 105 is provided in an upper portion of the display region 103. The imaging instruction button 105 is an on-off button. In a state in which the imaging instruction button 105 is off, the imaging instruction of the optical image 54 is not transmitted to the camera 20. For this reason, the optical image 54 is not displayed in the display region 103. On the other hand, in a case where the imaging instruction button 105 is turned on, the imaging instruction of the optical image 54 is transmitted to the camera 20, and as a result, the optical image 54 is displayed in the display region 103. The display control unit 79 displays the optical images 54 output from the camera 20 at the predetermined frame rate in the display region 104 while sequentially updating the optical images 54. That is, the optical image 54 that is displayed in the display region 104 is a live view image (video).

A spinal column shape derivation button 106 is provided in the display region 104. In a case where the spinal column shape derivation button 106 is selected, the processing shown in FIGS. 6 to 9, that is, the first extraction processing 90, the second extraction processing 92, the derivation processing 94, and the calculation processing of the Cobb angle are executed on the optical image 54 acquired by the first acquisition unit 75 at that moment in the extraction unit 76, the derivation unit 77, and the calculation unit 78. The display control unit 79 displays the obtained calculation result 87 in the display region 104.

The display control unit 79 displays a still image of the optical image 54 in a case where the spinal column shape derivation button 106 is selected, in the display region 103, and displays a polygonal line 107 representing the lines L5 to L7 of the polynomial of the spinal column shape information 86 to be superimposed on the optical image 54. The display control unit 79 displays a numerical value 109 of the first Cobb angle $\theta 1$ along with auxiliary lines 108 indicating the perpendicular lines PL1 and PL2, and a numerical value 111 of the second Cobb angle $\theta 2$ along with auxiliary lines 110 indicating the perpendicular lines PL2 and PL3 to be superimposed on the optical image 54.

In the display region 104, a store button 112 and a print button 113 are provided. In a case where the store button 112 is selected, the polynomial of the spinal column shape information 86 and the calculation result 87 are stored in the storage 55. The polynomial of the spinal column shape information 86 and the calculation result 87 stored in the storage 55 are registered in, for example, an electronic medical record of an electronic medical record system connected to the console 14 through a network. In a case where the print button 113 is selected, the contents (optical image 54, polygonal line 107, auxiliary lines 108 and 110, and numerical values 109 and 111) displayed in the display region 103 are printed on a paper medium. The paper medium is distributed to the subject H.

Figure 11:
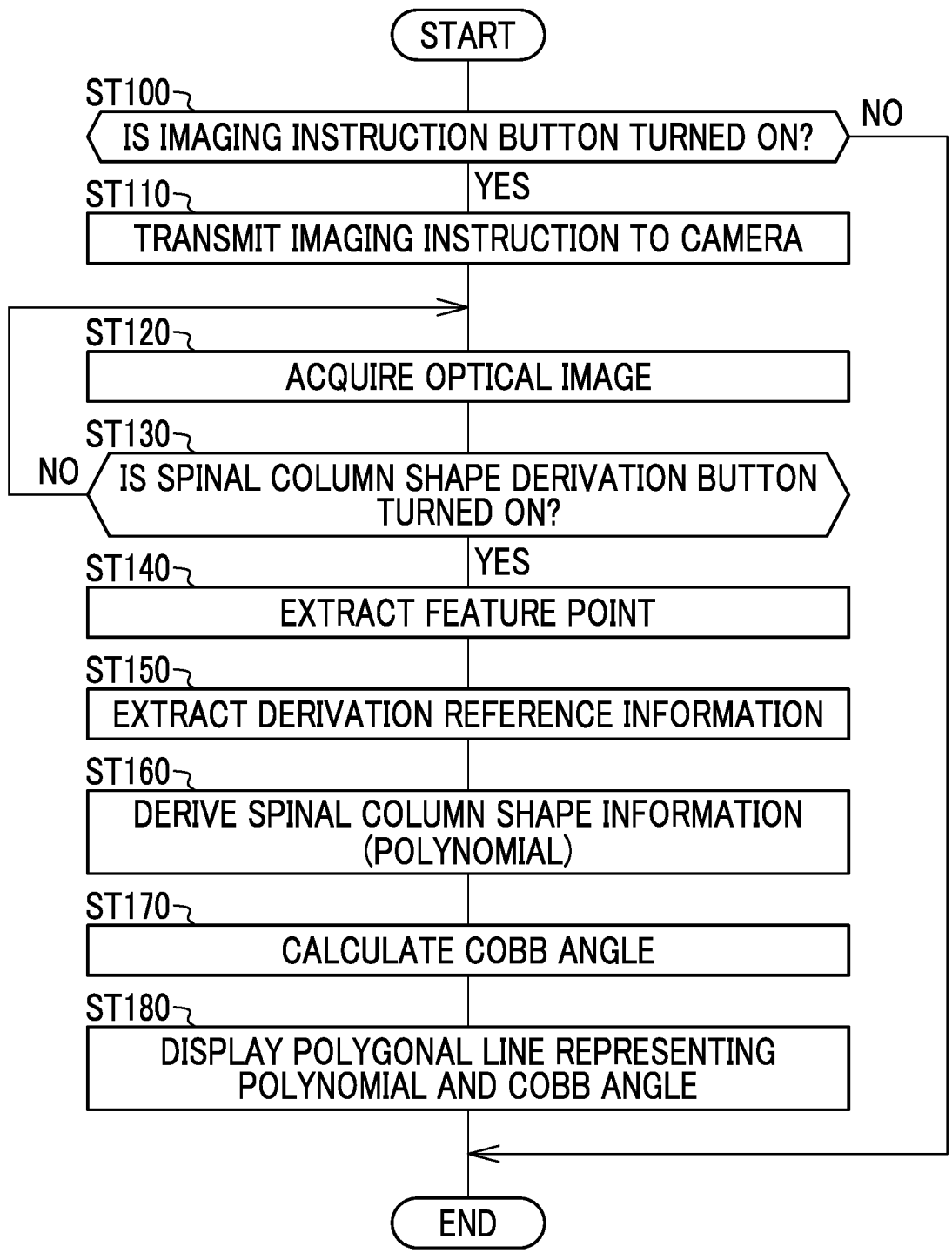
FIG. 11 is a flowchart illustrating a processing procedure of the console.

Next, the operations of the above-describe configuration will be described referring to a flowchart shown in FIG. 11 as an example. Prior to radiography, the operator OP performs imaging preparation work. The imaging preparation work includes the selection of the imaging menu 62, the setting of the irradiation condition 63 of the radiation R, positioning of the electronic cassette 13 and the radiation source 16 (adjustment of the height position and the SID), and positioning of the subject H (adjustment of a position and a posture with respect to the electronic cassette 13 and the radiation source 16). The operator OP operates the console 14 in the control room 26 to select the imaging menu 62 depending on radiography to be performed from now, and next, sets the irradiation condition 63 of the radiation R. Next, the operator OP sends an announcement to the speaker 30 to the waiting room 29 through the microphone 28 and guides the subject H from the waiting room 29 to the radiography room 25.

The operator OP sends an announcement to the speaker 27 of the radiography room 25 through the microphone 28 and makes the subject H stand before the upright imaging stand 12. The operator OP operates the console 14 to move up and down the holder 37 and the electronic cassette 13 conforming to the body height of the subject H and to adjust the height position of the electronic cassette 13. The operator OP operates the console 14 to move up and down the radiation source 16 and moves the radiation source 16 to a height position suitable for the height position of the electronic cassette 13. The operator OP operates the console 14 to move the radiation source 16 in parallel along the rail 48 and moves the radiation source 16 to a position of the SID depending on the selected imaging menu 62, in this case, "chest/upright/front".

The operator OP guides the subject H from the waiting room 29 to the radiography room 25, makes the subject H stand before the upright imaging stand 12, and turns on the imaging instruction button 105 of the information display screen 100 to ascertain the shape of the spinal column of the subject H by the optical image 54 (in Step ST100, YES). With this, the imaging instruction of the optical image 54 is transmitted from the console 14 to the camera 20 (Step ST110), and imaging of the optical image 54 is started in the camera 20.

In the console 14, the operation program 70 is started, so that the CPU 57 functions as the first acquisition unit 75, the extraction unit 76, the derivation unit 77, the calculation unit 78, and the display control unit 79. The optical image 54 from the camera 20 is acquired by the first acquisition unit 75 (Step ST120). The optical image 54 is output from the first acquisition unit 75 to the extraction unit 76 and the display control unit 79.

The operator OP makes the subject H stands directly in front of the upright imaging stand 12 while keeping the back straight, brings the posture of the subject H into a state appropriate for calculating the Cobb angle, and then, selects the spinal column shape derivation button 106 (in Step ST130, YES). With this, first, as shown in FIG. 6, the first extraction processing 90 is executed on the optical image 54 in the extraction unit 76. Then, the right and left shoulder joint points CP1 and CP2, the right and left hip joint points CP3 and CP4, the points CP5 and CP6 indicating the maximum width of the right and left armpits of the upper body, and the points CP7 and CP8 indicating the minimum width of the right and left armpits of the upper body of the subject H are extracted as the feature points (Step ST140).

Subsequently, the second extraction processing 92 is performed on the optical image 54 in the extraction unit 76. Then, the position coordinates OI_MP1(X,Y) of the middle point MP1 of the line L1 connecting the right and left shoulder joint points CP1 and CP2, the position coordinates OI_MP2(X,Y) of the middle point MP2 of the line L2 connecting the right and left hip joint points CP3 and CP4, the position coordinates OI_MP3(X,Y) of the middle point MP3 of the line L3 connecting the points CP5 and CP6 indicating the maximum width, and the position coordinates OI_MP4(X,Y) of the middle point MP4 of the line L4 connecting the points CP7 and CP8 indicating the minimum width are extracted as the derivation reference information 85 (Step ST150). The derivation reference information 85 is output from the extraction unit 76 to the derivation unit 77.

As shown in FIG. 8, in the derivation unit 77, the derivation processing 94 using the derivation reference information 85 is executed. With this, the polynomial representing the shape of the spinal column of the subject H is derived as the spinal column shape information 86 (Step ST160). The spinal column shape information 86 is output from the derivation unit 77 to the calculation unit 78 and the display control unit 79.

As shown in FIG. 9, in the calculation unit 78, the first Cobb angle θ1 and the second Cobb angle θ2 indicating the degree of curvature of the spinal column are calculated from the polynomial of the spinal column shape information 86 (Step ST170). The calculation result 87 of the first Cobb angle θ1 and the second Cobb angle θ2 is output from the calculation unit 78 to the display control unit 79.

As shown in FIG. 10, the polygonal line 107 representing the lines L5 to L7 of the polynomial of the spinal column shape information 86, the numerical value 109 of the first Cobb angle θ1, and the numerical value 111 of the second Cobb angle θ2 are displayed to be superimposed on the optical image 54 of the display region 103 of the information display screen 100 under the control of the display control unit 79. The calculation result 87 is displayed in the display region 104 (Step ST180). The operator OP selects the store button 112 and stores the polynomial of the spinal column shape information 86 and the calculation result 87 in the storage 55. The operator OP selects the print button 113, prints the contents displayed in the display region 103 on a paper medium, and distributes the paper medium to the subject H.

After the calculation of the Cobb angles, the operator OP sends an announcement to the speaker 27 of the radiography room 25 through the microphone 28. That is, the subject H is prompted to place the jaw on the holder 37, to set the hands on the hip and to thrust out the elbows, to open the shoulder bones to cover the holder 37 side, and to bring the chest into close contact with the holder 37. Next, the operator OP instructs the subject H to take a breath and to hold the breath. Thereafter, the operator OP operates the irradiation switch 19 to instruct the radiation source 16 to start the irradiation of the radiation R. With this, the irradiation of the radiation R from the radiation source 16 toward the subject H is performed.

The radiation R transmitted through the subject H reaches the electronic cassette 13. Then, the radiation R is detected as the radiographic image 66 by the electronic cassette 13. The radiographic image 66 is output from the electronic cassette 13 to the console 14. Then, in the console 14, various kinds of image processing are executed on the radiographic image 66 from the electronic cassette 13. Thereafter, the radiographic image 66 is displayed in the display region 103 of the information display screen 100 instead of the optical image 54.

As described above, the radiography system 2 comprises the radiation source 16 that irradiates the subject H with the radiation R, the camera 20, and the console 14. The camera 20 is provided in the radiation source 16. The camera 20 images the subject H irradiated with the illumination light 53 as light having uniform brightness to output the optical image 54. The CPU 57 of the console 14 has the first acquisition unit 75 and the derivation unit 77. The first acquisition unit 75 acquires the optical image 54 from the camera 20. The derivation unit 77 derives the spinal column shape information 86 representing the shape of the spinal column of the subject H based on the optical image 54.

In the technique of the present disclosure, only the camera 20 is provided in the radiation source 16, and unlike the moire fringe measurement apparatus described in JP6280676B, a large-scaled mechanism, such as the light projection unit that irradiates the back of the subject H with the light pattern for causing moire fringes, is not provided. Accordingly, it is possible to perform the ascertainment of the shape of the spinal column of the subject H based on the optical image 54 in conjunction with radiography without hindering the handling of the radiation source 16.

The extraction unit 76 extracts the feature points of the subject H from the optical image 54. The extraction unit 76 extracts the derivation reference information 85 for deriving the spinal column shape information 86 from the feature points. The derivation unit 77 derives the polynomial representing the shape of the spinal column as the spinal column shape information 86 based on the derivation reference information 85. In this way, first, the derivation reference information 85 is extracted after the feature points are extracted first, so that it is possible to increase the extraction accuracy of the derivation reference information 85, compared to a case where the derivation reference information 85 is extracted directly from the optical image 54. As a result, it is possible to increase the reliability of the polynomial of the spinal column shape information 86. With the polynomial, it is possible to allow the operator OP to easily ascertain the shape of the spinal column of the subject H.

The calculation unit 78 calculates the first Cobb angle θ1 and the second Cobb angle θ2 indicating the degree of curvature of the spinal column from the polynomial. The display control unit 79 performs control for displaying the numerical value 109 of the first Cobb angle θ1 and the numerical value 111 of the second Cobb angle θ2 to be superimposed on the optical image 54 of the display region 103 or for displaying the calculation result 87 of the first Cobb angle θ1 and the second Cobb angle θ2 in the display region 104 to display the first Cobb angle θ1 and the second Cobb angle θ2 on the display 40. With this, it is possible to allow the operator OP to easily ascertain the shape of the spinal column of the subject H. The operator OP progresses determination on whether or not a secondary medical examination of scoliosis by radiography is needed for the subject H.

The extraction unit 76 extracts the right and left shoulder joint points CP1 and CP2, the right and left hip joint points CP3 and CP4, the points CP5 and CP6 indicating the maximum width of the right and left armpits of the upper body, and the points CP7 and CP8 indicating the minimum width of the right and left armpits of the upper body of the subject H, as the feature points. Then, the extraction unit 76 extracts the position coordinates OI_MP1(X,Y) of the middle point MP1 of the line L1 connecting the right and left shoulder joint points CP1 and CP2, the position coordinates OI_MP2(X,Y) of the middle point MP2 of the line L2 connecting the right and left hip joint points CP3 and CP4, the position coordinates OI_MP3(X,Y) of the middle point MP3 of the line L3 connecting the points CP5 and CP6 indicating the maximum width, and the position coordinates OI_MP4(X,Y) of the middle point MP4 of the line L4 connecting the points CP7 and CP8 indicating the minimum width, as the derivation reference information 85. For this reason, the polynomial of the spinal column shape information 86 can be obtained with a simple arithmetic operation of substituting the position coordinates OI_MP1(X,Y) to OI_MP4(X,Y) of the respective middle points MP1 to MP4 into the basic polynomial to solve the equation.

The radiation source 16 is a ceiling suspension type. For this reason, in a case where a device that ascertains the shape of the spinal column of the subject H is provided and the weight of the radiation source 16 increases, there is a need for thickening the arm 45 to secure safety, and the handling of the radiation source 16 is hindered as much. In a case where the moire fringe measurement apparatus described in JP6280676B is provided in the radiation source 16, the weight is extremely heavy, and it is considered that the handling of the radiation source 16 is also considerably hindered. In the technique of the present disclosure, a device that ascertains the shape of the spinal column of the subject H is only the camera 20 of about several tens of g. For this reason, it may be considered that the handling of the radiation source 16 is not almost hindered.

Modification Example

Figure 12:
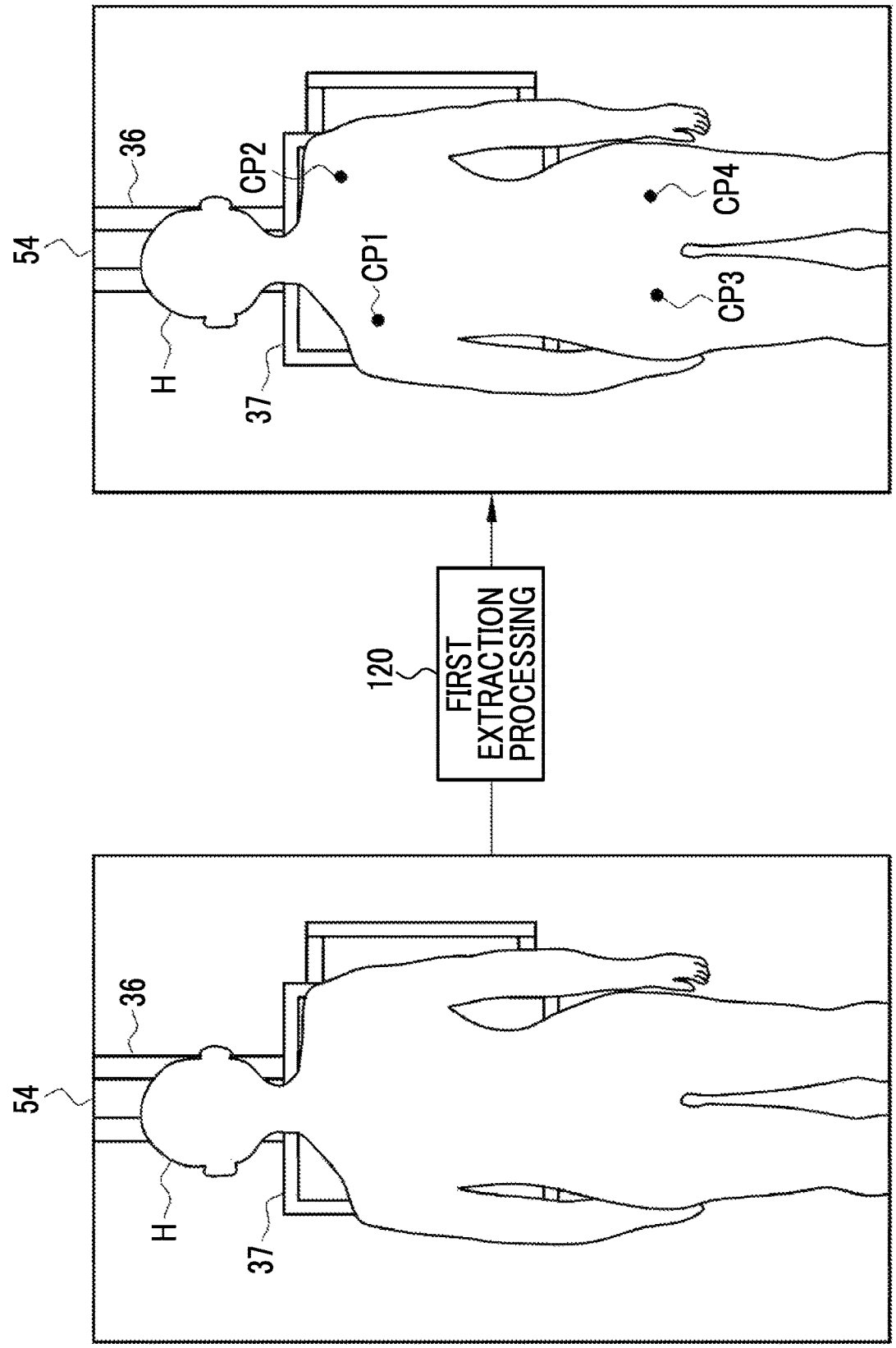
FIG. 12 is a diagram showing processing of the n extraction unit of a modification example.

As shown in FIG. 12 as an example, in the present modification example, the extraction unit 76 extracts the right and left shoulder joint points CP1 and CP2 and the right and left hip joint points CP3 and CP4 as the feature points in first extraction processing 120.

Figure 13:
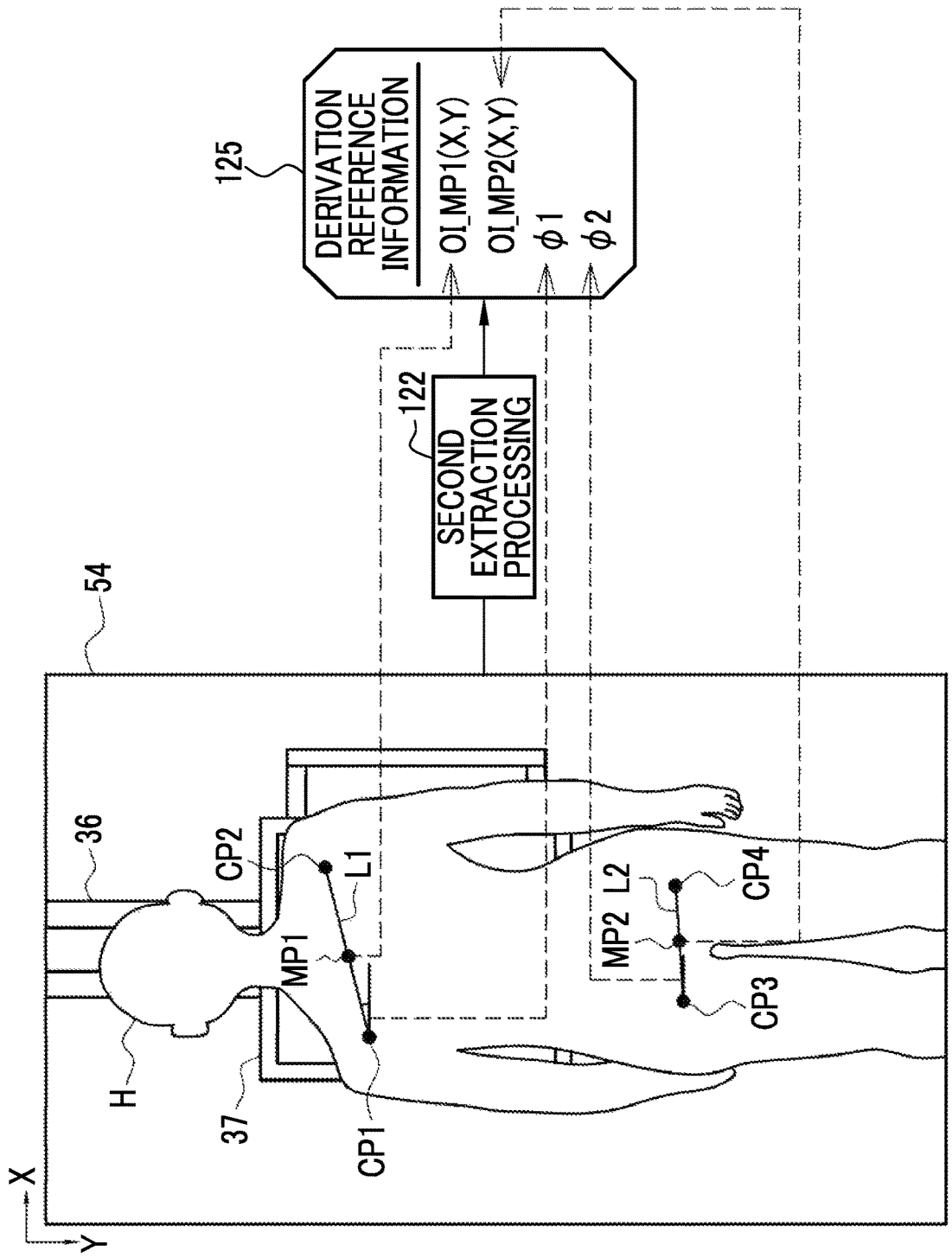
FIG. 13 is a diagram showing processing of the extraction unit of the modification example.

As shown in FIG. 13 as an example, in the present modification example, the extraction unit 76 extracts the position coordinates OI_MP1(X,Y) of the middle point MP1 of the line L1 connecting the right and left shoulder joint points CP1 and CP2, the position coordinates OI_MP2(X,Y) of the middle point MP2 of the line L2 connecting the right and left hip joint points CP3 and CP4, an inclination φ1 of the line L1 connecting the right and left shoulder joint points CP1 and CP2, and an inclination φ2 of the line L2 connecting the right and left hip joint points CP3 and CP4, as derivation reference information 125 in second extraction processing 122. Even with the derivation reference information 125, the polynomial of the spinal column shape information 86 can be obtained. The number of feature points to be extracted is reduced compared to the above-described first embodiment, and a load of the first extraction processing 120 can be reduced. The inclination φ1 can be replaced with an angle between the line L1 connecting the right and left shoulder joint points CP1 and CP2 and the X axis. Similarly, the inclination φ2 can be replaced with an angle between the line L2 connecting the right and left hip joint points CP3 and CP4 and the X axis.

In this way, the feature points extracted from the optical image 54 and the derivation reference information extracted from the feature points are not limited to the points CP1 to CP8 illustrated in the first embodiment and the derivation reference information 85.

The basic polynomial is not limited to the illustrated cubic polynomial. A quadratic polynomial may be employed. A fourth-degree or higher polynomial may be employed. The degree of the polynomial may be changed depending on the subject H. In a case of a fourth-degree or higher polynomial, there is a need for further extracting middle points MP of which position coordinates are registered in the derivation reference information 85, and feature points for extracting the middle points MP.

The operator OP may attach marks to the feature points, such as the right and left shoulder joint points, and image recognition is performed on the marks shown in the optical image 54 to extract the feature points. Similarly, the operator OP may attach marks to a few of vertebral bodies, image recognition is performed on the marks shown in the optical image 54 to extract the vertebral bodies, and position coordinates of the extracted vertebral bodies may be included in the derivation reference information 85.

Second Embodiment

Figure 14:
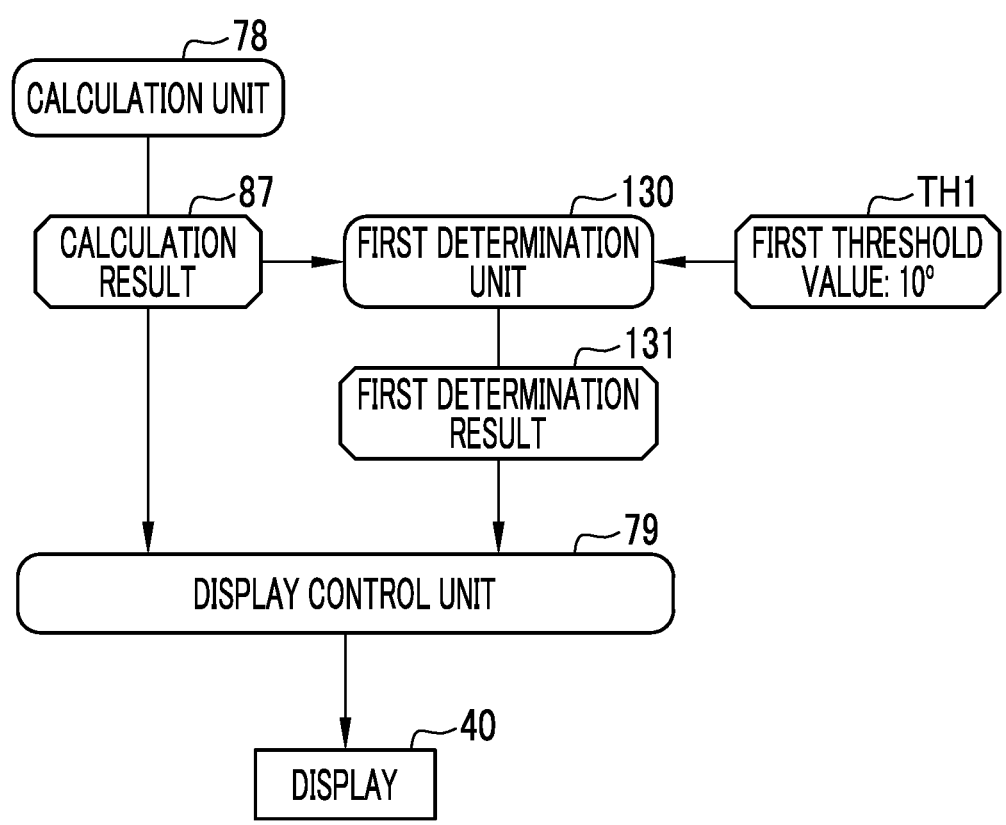
FIG. 14 is a diagram showing a second embodiment in which determination is made on whether or not a secondary medical examination of scoliosis by radiography is needed for a subject.

As shown in FIG. 14 as an example, a CPU 57 of a console 14 of a second embodiment functions as a first determination unit 130, in addition to the processing units 75 to 79 (the units other than the calculation unit 78 and the display control unit 79 are not shown) of the above-described first embodiment.

The calculation result 87 from the calculation unit 78 is input to the first determination unit 130. The first determination unit 130 determines whether or not a secondary medical examination of scoliosis by radiography is needed for the subject H, by comparing the first Cobb angle θ1 and the second Cobb angle θ2 of the calculation result 87 with a first threshold value TH1 set in advance. The first determination unit 130 outputs a first determination result 131 regarding whether or not the secondary medical examination is needed, to the display control unit 79.

In FIG. 14, 10° is set as the first threshold value TH1. A numerical value "10°" is a value of a Cobb angle with which scoliosis of the spinal column is generally diagnosed.

Figure 15A:
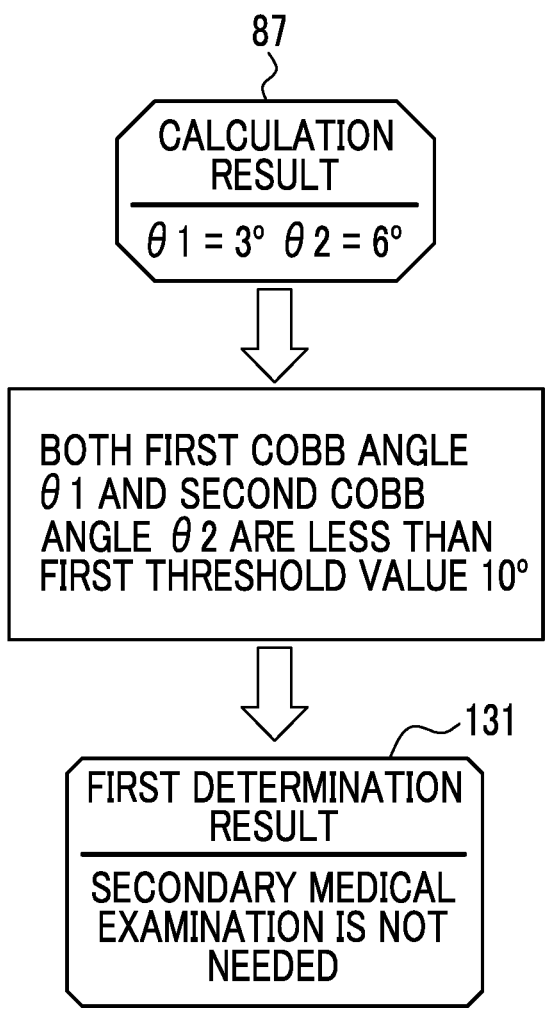
FIGS. 15A and 15B are diagrams showing processing of a first determination unit.
Figure 15B:
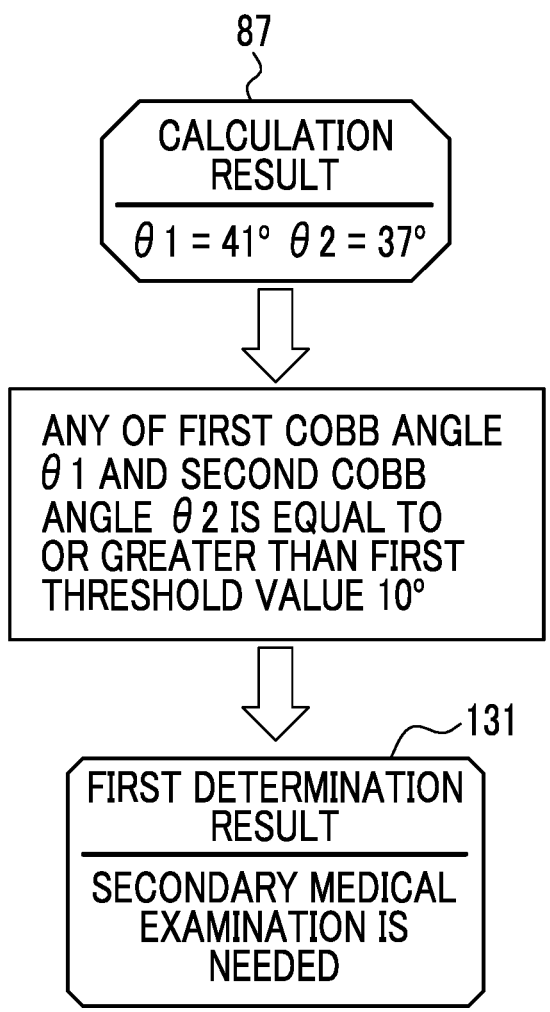

As shown in FIGS. 15A and 15B as an example, the first determination unit 130 determines whether or not the secondary medical examination is needed, depending on whether or not the first Cobb angle θ1 and the second Cobb angle θ2 of the calculation result 87 are less than the first threshold value TH1. As shown in FIG. 15A, in a case where both the first Cobb angle θ1 and the second Cobb angle θ2 of the calculation result 87 are less than the first threshold value TH1 of 10°, the first determination unit 130 determines that the secondary medical examination is not needed, and outputs a first determination result 131 indicating that the secondary medical examination is not needed. On the other hand, as shown in FIG. 15B, in a case where any of the first Cobb angle θ1 and the second Cobb angle θ2 of the calculation result 87 is equal to or greater than the first threshold value TH1 of 10°, the first determination unit 130 determines that the secondary medical examination is needed, and outputs a first determination result 131 indicating that the secondary medical examination is needed.

Figure 16:
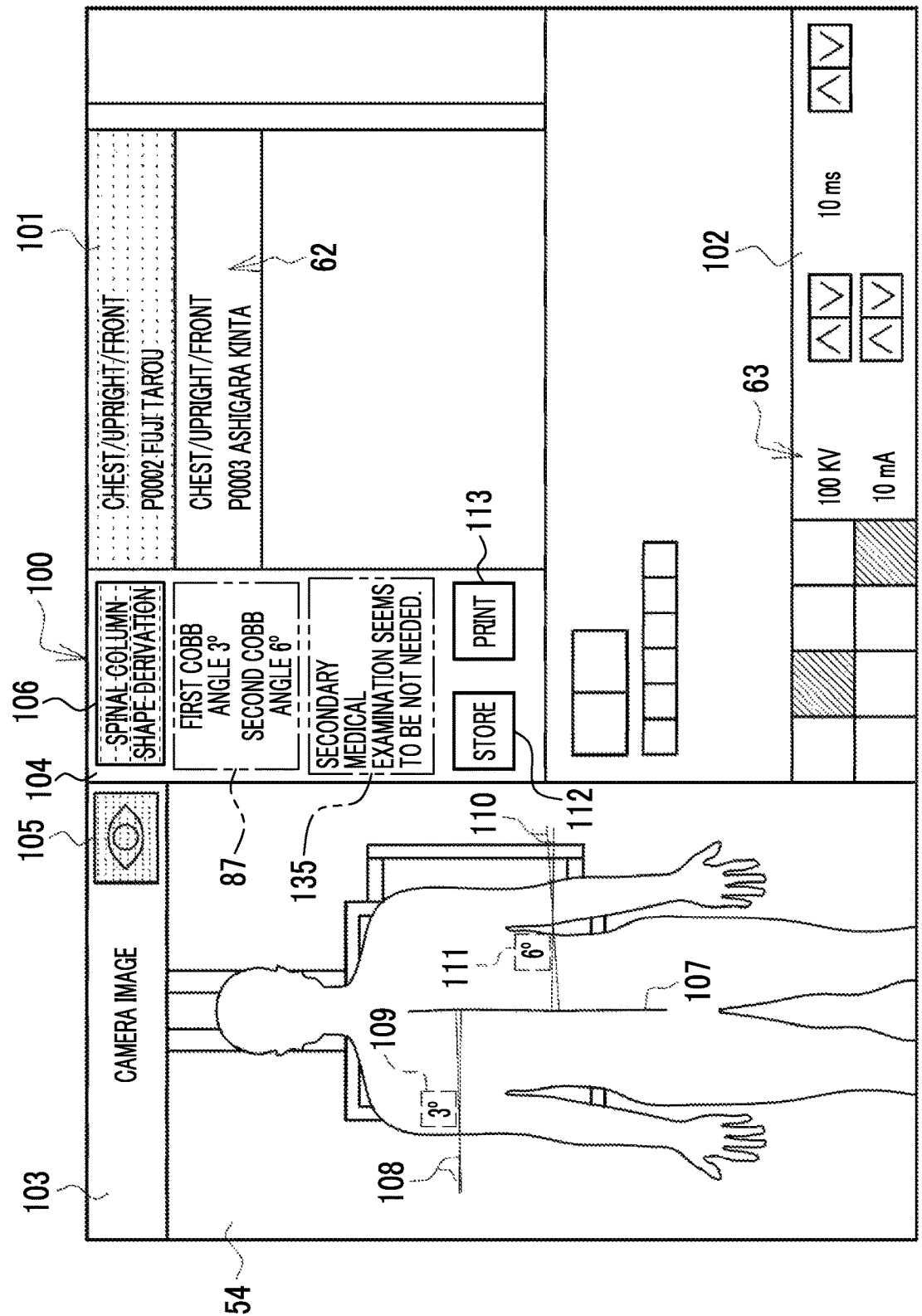
FIG. 16 is a diagram showing the information display screen in a case where both the first Cobb angle and the second Cobb angle are less than the first threshold value.

FIG. 16 shows the information display screen 100 in a case where, in the determination shown in FIGS. 15A and 15B, both the first Cobb angle θ1 and the second Cobb angle θ2 of the calculation result 87 are less than the first threshold value TH1, and the first determination result 131 indicating that the secondary medical examination is not needed is obtained (a case of FIG. 15A). In this case, the display control unit 79 displays a message 135 indicating that the secondary medical examination is not needed, in the display region 104. The operator OP sends an announcement to the speaker 27 of the radiography room 25 through the microphone 28 and notifies the subject H that the secondary medical examination is not needed.

Figure 17:
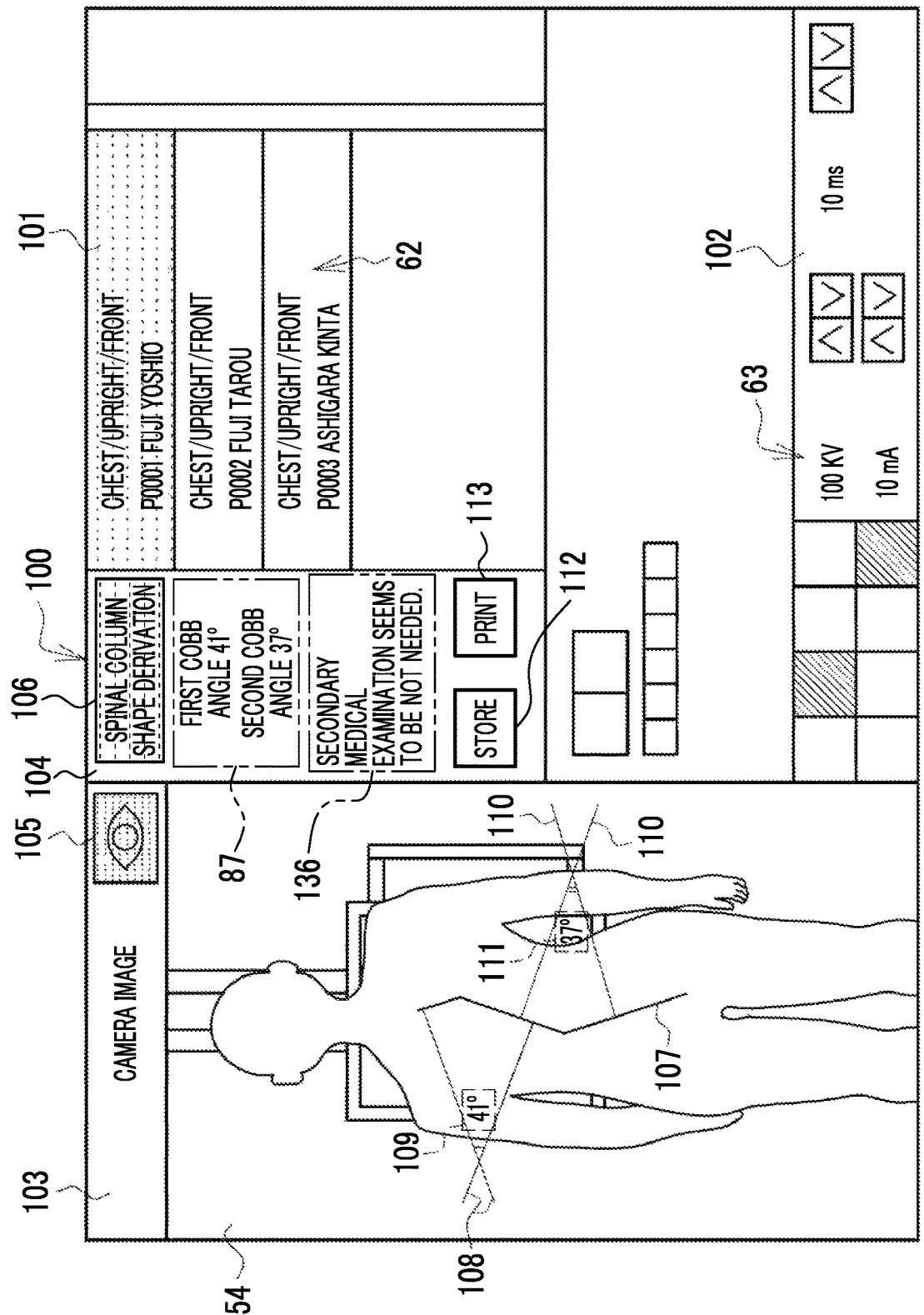
FIG. 17 is a diagram showing the information display screen in a case where any of the first Cobb angle and the second Cobb angle is equal to or greater than the first threshold value.

On the other hand, FIG. 17 shows the information display screen 100 in a case where, in the determination shown in FIGS. 15A and 15B, any of the first Cobb angle θ1 and the second Cobb angle θ2 of the calculation result 87 is equal to or greater than the first threshold value TH1, and the first determination result 131 indicating that the secondary medical examination is needed is obtained (a case of FIG. 15B). In this case, the display control unit 79 displays a message 136 indicating the secondary medical examination is needed, in the display region 104. The operator OP sends an announcement to the speaker 27 of the radiography room 25 through the microphone 28 and notifies the subject H that the secondary medical examination is needed.

In this way, in the second embodiment, the first determination unit 130 determines whether or not the secondary medical examination of scoliosis by radiography is needed for the subject H, based on the first Cobb angle θ1 and the second Cobb angle θ2. The display control unit 79 displays the message 135 or 136 in the display region 104 to perform control for displaying the first determination result 131 of the first determination unit 130 on the display 40. For this reason, the operator OP can simply know whether or not the secondary medical examination is needed for the subject H, and can instantly notify the subject H whether or not the secondary medical examination is needed.

The superimposition display of the numerical value 109 of the first Cobb angle θ1 and the numerical value 111 of the second Cobb angle θ2 on the optical image 54 and the display of the calculation result 87 of the first Cobb angle θ1 and the second Cobb angle θ2 in the display region 104 may be omitted, and the message 135 or 136 may be just displayed in the display region 104.

Instead of or in addition to displaying the first determination result 131 through the information display screen 100, the first determination result 131 may be notified by voice. The first determination result 131 may be notified by an indicator, such as a warning lamp.

Third Embodiment

Figure 18:
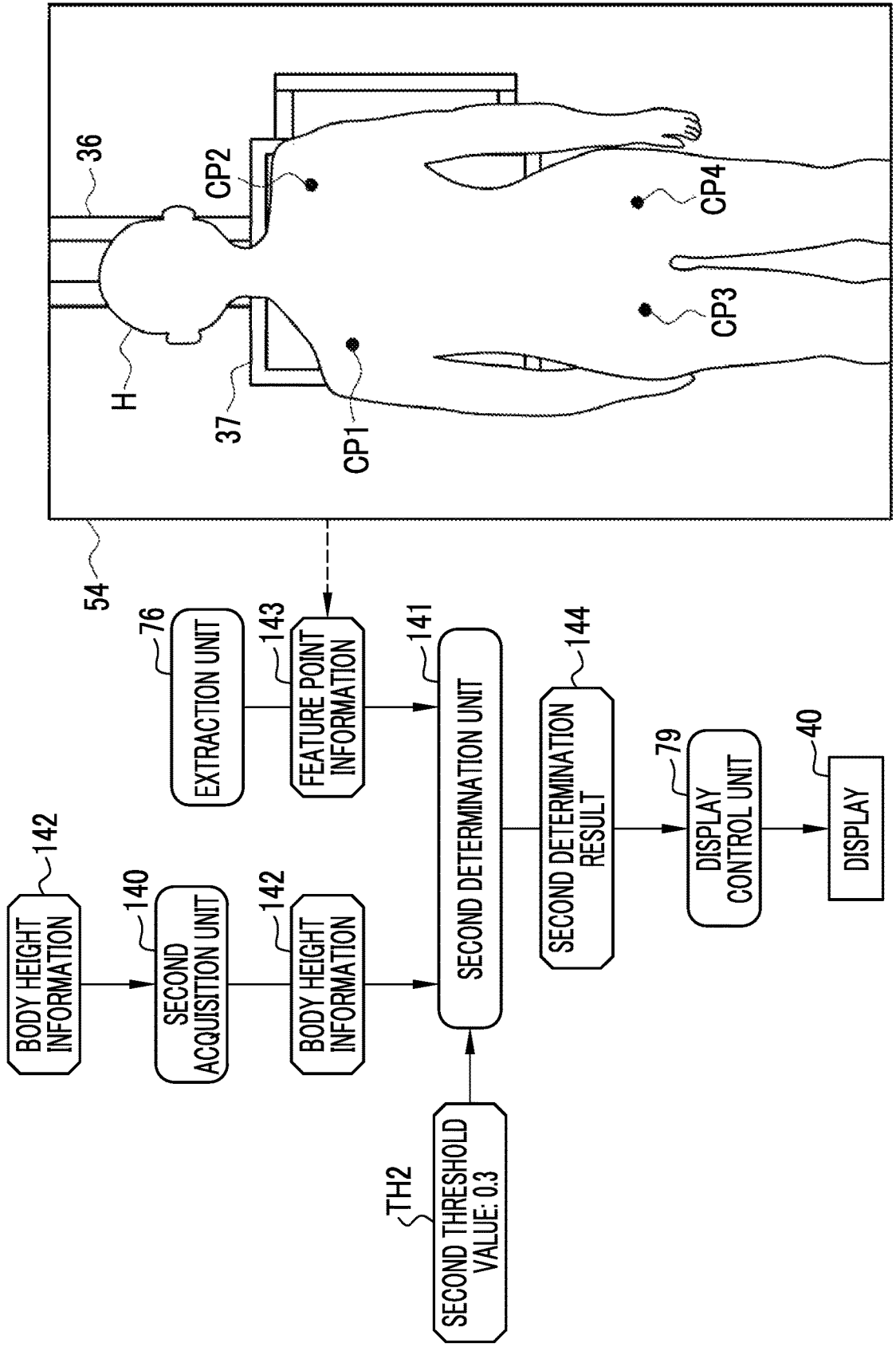
FIG. 18 is a diagram showing a third embodiment in which determination is made on whether or not derivation of spinal column shape information based on an optical image is needed.

As shown in FIG. 18 as an example, a CPU 57 of a console 14 of a third embodiment functions as a second acquisition unit 140 and a second determination unit 141, in addition to the processing units 75 to 79 (the units other than the extraction unit 76 and the display control unit 79 are not shown) of the above-described first embodiment.

The second acquisition unit 140 acquires body height information 142 that is information regarding a body height of the subject H. The second acquisition unit 140 outputs the body height information 142 to the second determination unit 141. The body height information 142 may be input by the operator OP through the input device 41 or may be estimated from a height of the subject H shown in the optical image 54. The body height information 142 may be estimated from a height position of the holder 37 of the upright imaging stand 12 or a height position of the radiation source 16 after being adjusted conforming to the body height of the subject H. Alternatively, a scale representing a body height may be provided in a field of view FOV of the optical image 54, such as the support 36 of the upright imaging stand 12 or a wall of the radiography room 25 in the vicinity of the upright imaging stand 12, and image recognition may be performed on divisions of the scale shown in the optical image 54.

In addition to the body height information 142 from the second acquisition unit 140, feature point information 143 is input from the extraction unit 76 to the second determination unit 141. The feature point information 143 is position coordinates of the right and left shoulder joint points CP1 and CP2 and position coordinates of the right and left hip joint points CP3 and CP4 as the feature points extracted by the extraction unit 76 through the first extraction processing 90 or 120. The second determination unit 141 determines whether or not the derivation of the spinal column shape information 86 based on the optical image 54 is needed, based on the body height information 142, the feature point information 143, and a second threshold value TH2 set in advance. The second determination unit 141 performs the determination before the imaging instruction button 105 is turned on and the spinal column shape derivation button 106 is selected. The second determination unit 141 outputs a second determination result 144 regarding whether or not the derivation of the spinal column shape information 86 based on the optical image 54 is needed, to the display control unit 79.

In FIG. 18, 0.3 is set as the second threshold value TH2. A numerical value "0.3" is a value statistically obtained from data of an unspecified large number of subjects H in the past. The numerical value of the second threshold value TH2 may be changed depending on an attribute of the subject H, such as sex, age, or body type.

Figure 19:
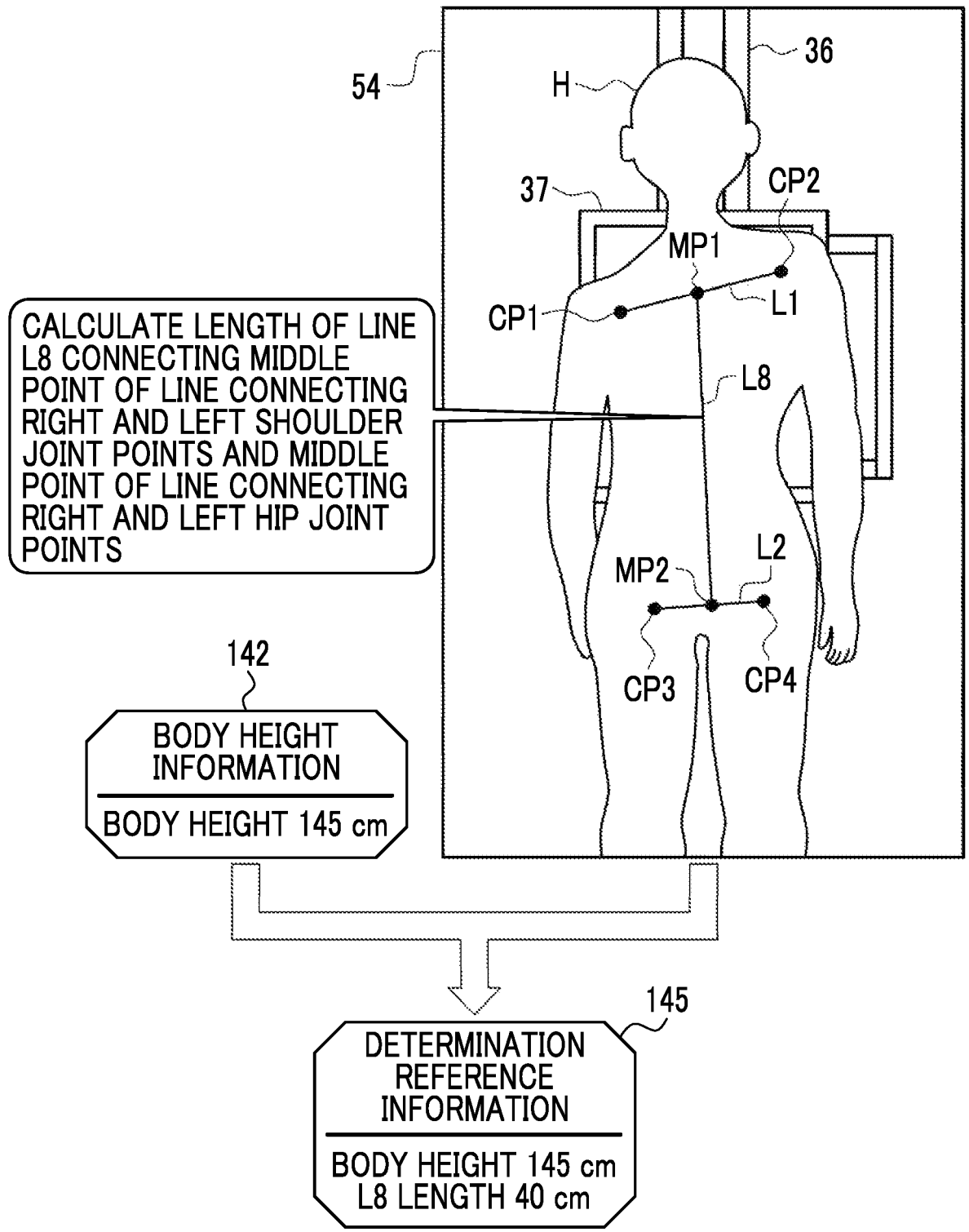
FIG. 19 is a diagram showing processing of a second determination unit.

As shown in FIG. 19 as an example, the second determination unit 141 calculates a length of a line L8 that connects the middle point MP1 of the line L1 connecting the right and left shoulder joint points CP1 and CP2 and the middle point MP2 of the line L2 connecting the right and left hip joint points CP3 and CP4, based on the feature point information 143. Then, the calculated length of the line L8 is converted into a length on a real space depending on the SID and the FOV of the camera 20. The second determination unit 141 combines the obtained length of the line L8 on the real space and the body height of the body height information 142 as determination reference information 145.

Figure 20A:
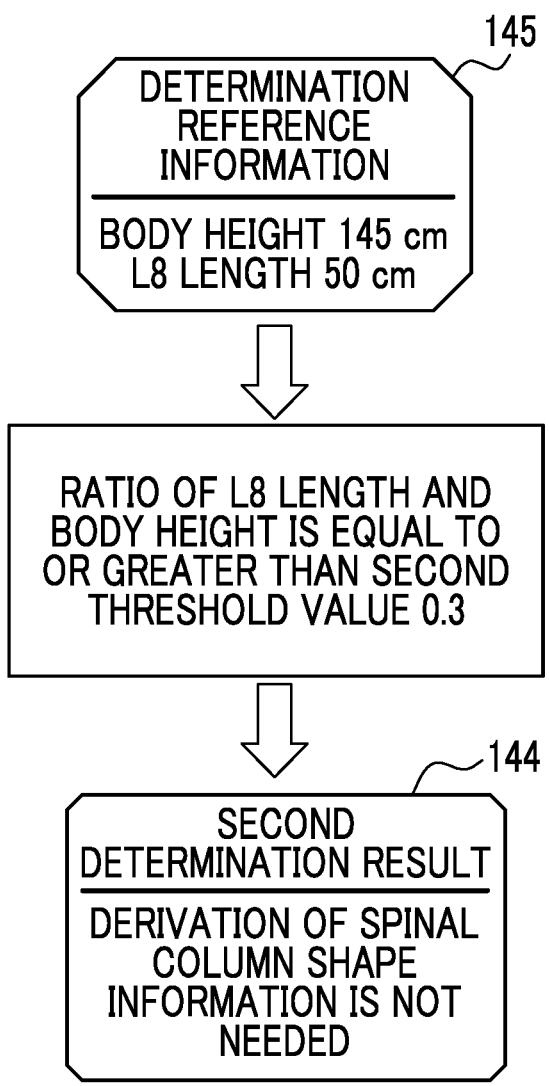
FIGS. 20A and 20B are diagrams showing processing of the second determination unit.
Figure 20B:
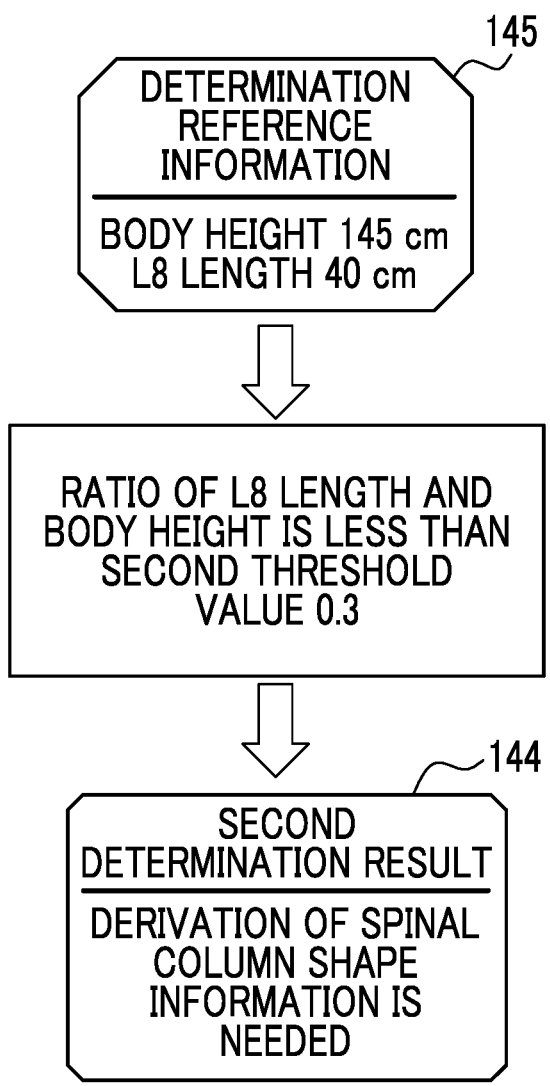

As shown in FIGS. 20A and 20B as an example, the second determination unit 141 determines whether or not the derivation of the spinal column shape information 86 based on the optical image 54 is needed, depending on whether or not a ratio of the length of the line L8 and the body height is equal to or greater than the second threshold value TH2. This determination method is based on knowledge that, in a case where the spinal column has scoliosis, the length of the line L8 with respect to the body height is shorter than a healthy person.

As shown in FIG. 20A, in a case where the ratio (50 cm/145 cm≈0.34) of the length of the line L8 and the body height of the determination reference information 145 is equal to or greater than the second threshold value TH2 of 0.3, the second determination unit 141 determines that the derivation of the spinal column shape information 86 based on the optical image 54 is not needed, and outputs the second determination result 144 indicating that the derivation of the spinal column shape information 86 is not needed. On the other hand, as shown in FIG. 20B, in a case where the ratio (40 cm/145 cm≈0.28) of the length of the line L8 and the body height of the determination reference information 145 is less than the second threshold value TH2 of 0.3, the second determination unit 141 determines that the derivation of the spinal column shape information 86 based on the optical image 54 is needed, and outputs the second determination result 144 indicating that the derivation of the spinal column shape information 86 is needed.

Figure 21:
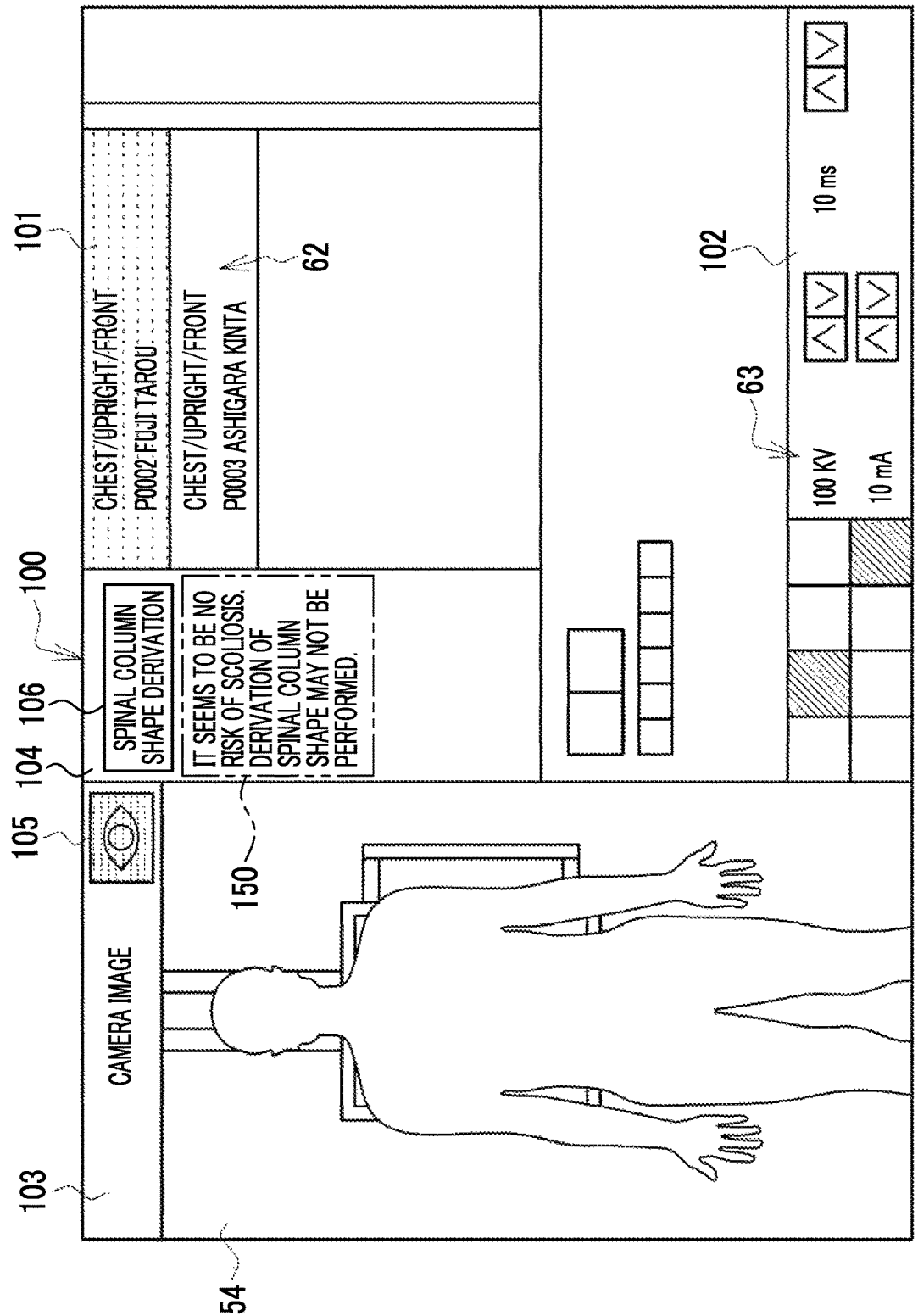
FIG. 21 is a diagram showing the information display screen in a case where the ratio of the length of the line that connects the middle point of the line connecting the right and left shoulder joint points and the middle point of the line connecting the right and left hip joint points, to the body height is equal to or greater than the second threshold value.

FIG. 21 shows the information display screen 100 in a case where, in the determination shown in FIGS. 20A and 20B, the ratio of the length of the line L8 and the body height of the determination reference information 145 is equal to or greater than the second threshold value TH2, and the second determination result 144 indicating that the derivation of the spinal column shape information 86 based on the optical image 54 is not needed is obtained (a case of FIG. 20A). In this case, the display control unit 79 displays a message 150 indicating that there is no concern of scoliosis in the subject H, and the derivation of the spinal column shape information 86 is not needed, in the display region 104. The operator OP immediately proceeds to radiography without selecting the spinal column shape derivation button 106.

Figure 22:
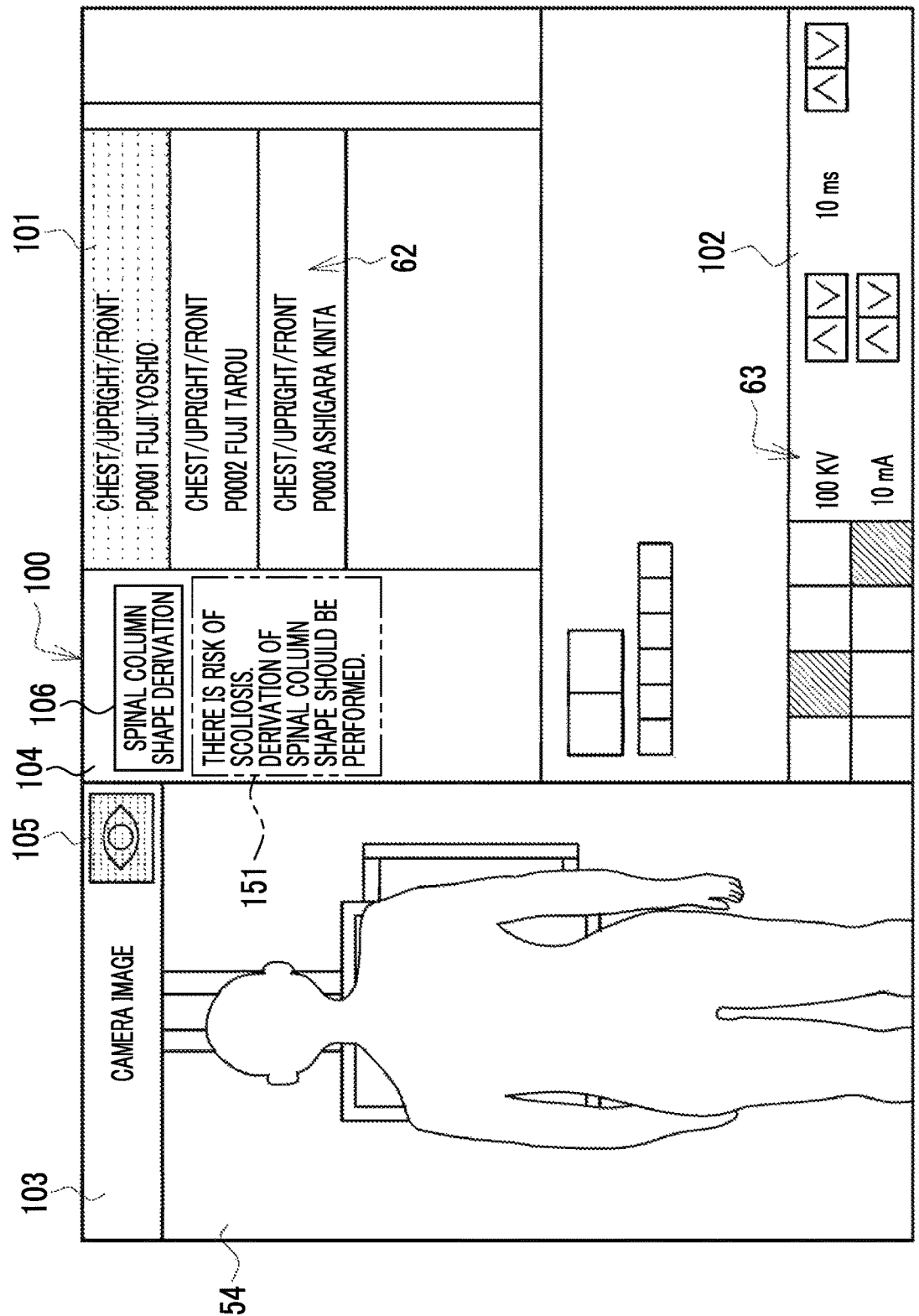
FIG. 22 is a diagram showing the information display screen in a case where the ratio of the length of the line that connects the middle point of the line connecting the right and left shoulder joint points and the middle point of the line connecting the right and left hip joint points, to the body height is less than the second threshold value.

On the other hand, FIG. 22 shows the information display screen 100 in a case where, in the determination shown in FIGS. 20A and 20B, the ratio of the length of the line L8 and the body height of the determination reference information 145 is less than the second threshold value TH2, and the second determination result 144 indicating that the derivation of the spinal column shape information 86 based on the optical image 54 is needed is obtained (a case of FIG. 20B). In this case, the display control unit 79 displays a message 151 indicating that there is a concern of scoliosis in the subject H, and the derivation of the spinal column shape information 86 is needed, in the display region 104. The operator OP selects the spinal column shape derivation button 106 and makes the CPU 57 perform the derivation of the spinal column shape information 86.

In this way, in the third embodiment, prior to the derivation of the spinal column shape information 86 based on the optical image 54, the second acquisition unit 140 acquires the body height information 142 of the subject H. The extraction unit 76 extracts the right and left shoulder joint points CP1 and CP2 and the right and left hip joint points CP3 and CP4 of the subject H, as the feature points. The second determination unit 141 determines whether or not the derivation of the spinal column shape information 86 based on the optical image 54 is needed, based on the body height of the subject and the length of the line L8 that connects the middle point MP1 of the line L1 connecting the right and left shoulder joint points CP1 and CP2 and the middle point MP2 of the line L2 connecting the right and left hip joint points CP3 and CP4. The display control unit 79 displays the message 150 or 151 in the display region 104 to perform control for displaying the second determination result 144 of the second determination unit 141 in the display 40. For this reason, it is possible to selectively derive the spinal column shape information 86 of the subject H who has a risk of scoliosis, and to eliminate a waste of labor for deriving spinal column shape information 86 of the subject H who has no risk of scoliosis, on purpose.

In a case where the second determination result 144 that the derivation of the spinal column shape information 86 based on the optical image 54 is not needed is obtained, the spinal column shape derivation button 106 itself may not be displayed in the display region 104 or the spinal column shape derivation button 106 may be grayed out to be unselectable such that the derivation of the spinal column shape information 86 cannot be performed.

In a case where the operator OP selects the spinal column shape derivation button 106, the determination by the second determination unit 141 may be performed. In this case, in a case where the second determination result 144 that the derivation of the spinal column shape information 86 based on the optical image 54 is not needed is obtained, the message 150 is displayed in the display region 104. On the other hand, in a case where the second determination result 144 that the derivation of the spinal column shape information 86 based on the optical image 54 is needed is obtained, the CPU 57 is made to perform the derivation of the spinal column shape information 86 without displaying the message 151 in the display region 104.

Instead of or in addition to displaying the second determination result 144 through the information display screen 100, the second determination result 144 may be notified by voice. The second determination result 144 may be notified by an indicator, such as a warning lamp.

Fourth Embodiment

Figure 23:
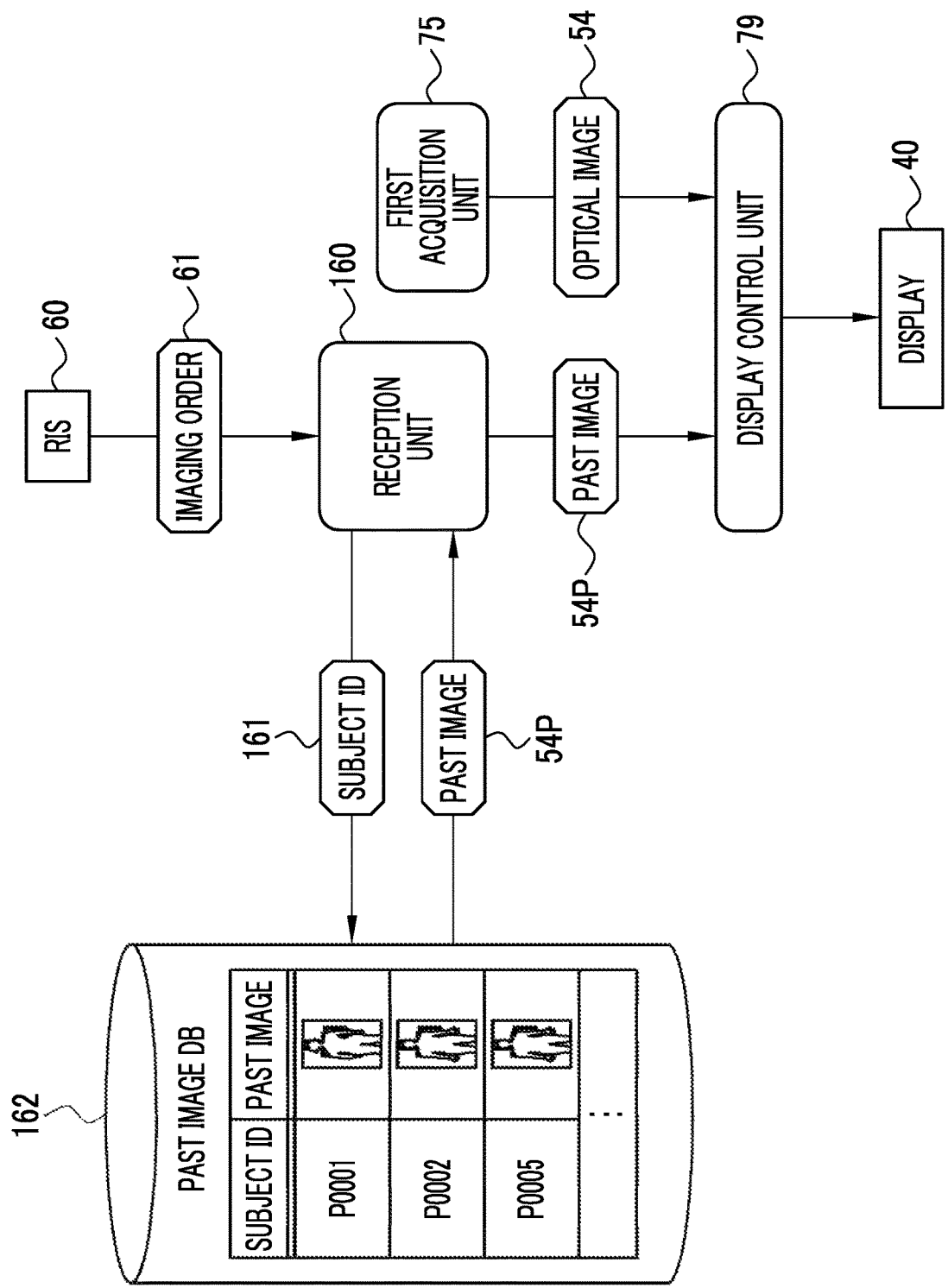
FIG. 23 is a diagram showing a fourth embodiment in which control for displaying a past optical image on a display to be superimposed on a current optical image is performed.

As shown in FIG. 23 as an example, a CPU 57 of a console 14 of a fourth embodiment functions as a reception unit 160, in addition to the processing units 75 to 79 (the units other than the first acquisition unit 75 and the display control unit 79 are not shown) of the above-described first embodiment.

The reception unit 160 receives the imaging order 61 from the RIS 60. The reception unit 160 outputs the subject ID 161 included in the imaging order 61 to a past image database (hereinafter, referred to as a data base (DB)) 162. In the past image DB 162, a set of the subject ID 161 of the subject H subjected to the derivation of the spinal column shape information 86 based on the optical image 54 in the past with the radiography system 2, and a past image 54P that is a past optical image 54 obtained by imaging the subject H having the subject ID 161 with the camera 20 at the time of the past derivation of the spinal column shape information 86 is stored. The past image 54P is one still image captured with the camera 20 at the time of the last derivation of the spinal column shape information 86.

The past image DB 162 receives the subject ID 161 from the reception unit 160, reads out the past image 54P corresponding to the subject ID 161, and transmits the read-out past image 54P to the reception unit 160. The reception unit 160 outputs the past image 54P to the display control unit 79. In a case where the subject ID 161 from the reception unit 160 is not registered, the past image DB 162 transmits the effect that the subject ID 161 is not registered, to the reception unit 160.

Figure 24:
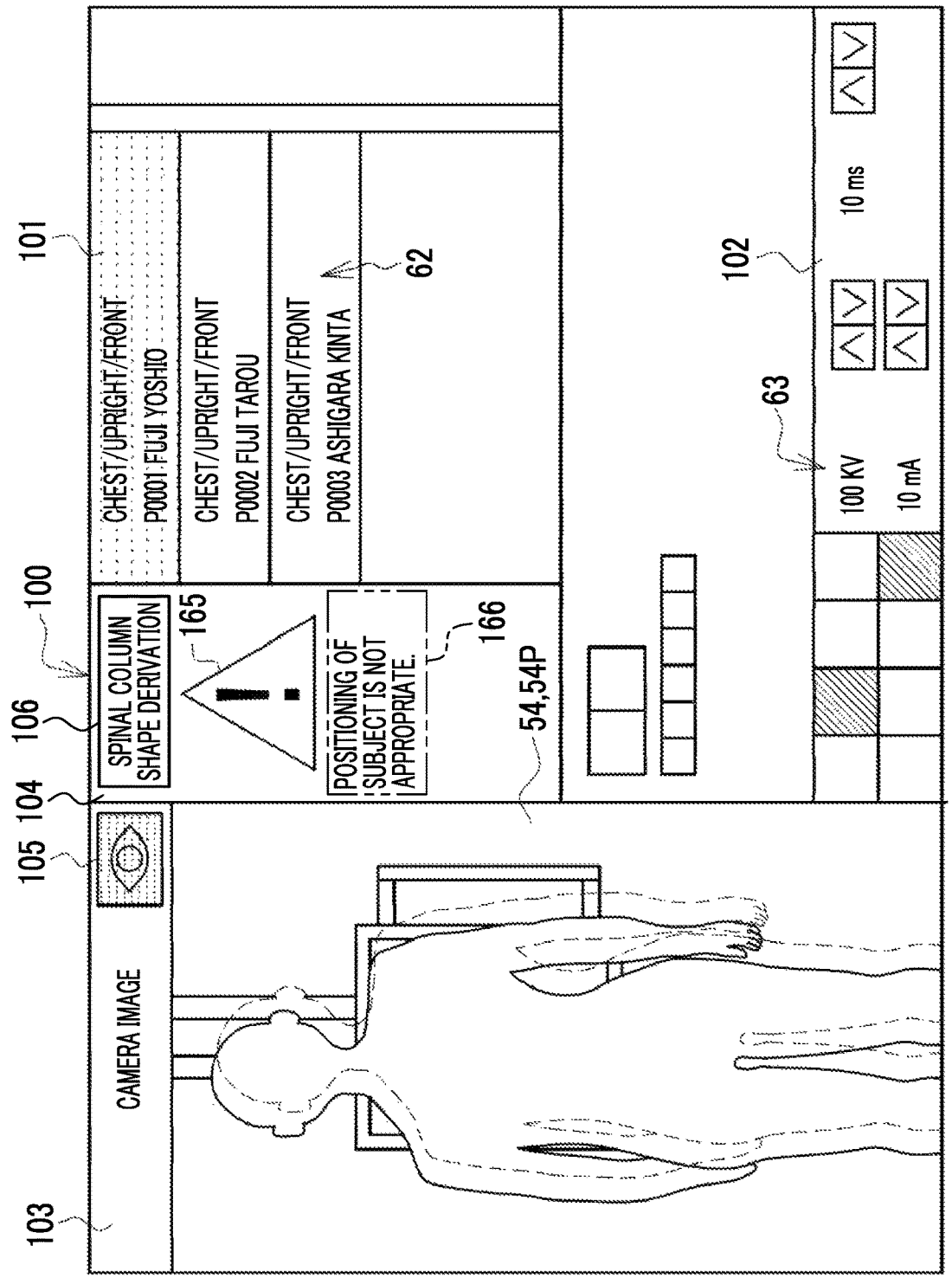
FIG. 24 is a diagram showing the information display screen on which the past optical image is displayed to be superimposed on the current optical image.

As shown in FIG. 24 as an example, the display control unit 79 displays the current optical image 54 of video and the past image 54P as a still image in the display region 103 in a superimposed manner at the time of imaging preparation before the derivation of the spinal column shape information 86. The time of imaging preparation before the derivation of the spinal column shape information 86 is specifically before the imaging instruction button 105 is turned on and the spinal column shape derivation button 106 is selected. As indicated by a broken line, the past image 54P is displayed with transparency of, for example, 50%. In a case where the effect that the subject ID 161 is not registered is received by the reception unit 160, a dialog box including a message indicating that there is no past image 54P is pop-up displayed on the information display screen 100.

FIG. 24 illustrates a case where a position of the subject H shown in the current optical image 54 and a position of the subject H shown in the past image 54P are separated by a threshold value or more. In this case, an exclamation mark 165, and a message 166 indicating that the positioning of the subject H is not appropriate are displayed in the display region 104.

Determination on whether or not the position of the subject H shown in the current optical image 54 and the position of the subject H shown in the past image 54P are separated by the threshold value or more is performed as follows, for example. That is, the first extraction processing 90 or 120 is executed on each of the current optical image 54 and the past image 54P. Then, a distance (for example, a distance between the left shoulder joint points CP1) between a feature point of the current optical image 54 and a feature point of the past image 54P is calculated, and the calculation distance is compared with a threshold value set in advance.

In this way, in the fourth embodiment, in a case of performing again the derivation of the spinal column shape information 86 on the subject H subjected to the derivation of the spinal column shape information 86 based on the optical image 54 in the past, the display control unit 79 performs control for displaying the past image 54P as a past optical image acquired in the past on the display 40 to be superimposed on the current optical image 54 at the time of imaging preparation before the derivation of the spinal column shape information 86. For this reason, the operator OP can easily confirm how much the current position of the subject H deviates from the past position of the subject H. The operator OP can instruct the subject H to correct positioning to eliminate the deviation from the past position and can easily conform the current position of the subject H to the past position of the subject H. Accordingly, it is possible to secure the reproducibility of the spinal column shape information 86. In a case where treatment of scoliosis is performed on the subject H, it is possible to correctly make sure of the effect of the treatment.

Instead of or in addition to displaying the effect that the positioning of the subject H is not appropriate, through the information display screen 100, the effect that the positioning of the subject H is not appropriate may be notified by voice. The effect that the positioning of the subject H is not appropriate may be notified by an indicator, such as a warning lamp.

A pressure sensor-equipped mat may be provided on the floor surface of the radiography room 25 below the upright imaging stand 12, and determination may be made on whether or not the subject H is standing in front of the upright imaging stand 12, based on a measurement result of the pressure sensor. Determination may be made on whether or not the subject H is standing in front of the upright imaging stand 12, from the optical image 54. Then, in a case where determination is made that the subject H is not standing in front of the upright imaging stand 12, a warning may be displayed or the irradiation of the radiation R may be prohibited. The body movement of the subject H may be detected from the optical image 54, and in a case where a body movement amount is equal to or greater than a threshold value set in advance, a warning may be displayed or the irradiation of the radiation R may be prohibited.

The first Cobb angle $\theta 1$ and the second Cobb angle $\theta 2$ may also be calculated from the radiographic image 66. In this case, the first Cobb angle $\theta 1$ and the second Cobb angle $\theta 2$ calculated from the radiographic image 66, and the first Cobb angle $\theta 1$ and the second Cobb angle $\theta 2$ calculated from the optical image 54 may be displayed to be comparable. Alternatively, at the time of the secondary medical examination of scoliosis by radiography, the first Cobb angle $\theta 1$ and the second Cobb angle $\theta 2$ calculated from radiographic image obtained in the secondary medical examination, and the first Cobb angle $\theta 1$ and the second Cobb angle $\theta 2$ calculated from the optical image 54 may be displayed to be comparable. Then, it is possible to confirm the validity of the first Cobb angle $\theta 1$ and the second Cobb angle $\theta 2$ calculated from the optical image 54.

Although the electronic cassette 13 is illustrated as a radiographic image detector, the technique of the present disclosure is not limited thereto. A radiographic image detector that is installed to the upright imaging stand 12 may be employed. The radiation source 16 may be a type of being attached to a support provided to be movable in parallel to the floor surface of the radiography room 25, not a ceiling suspension type.

A display may be attached to the upright imaging stand 12, and various screens, such as the information display screen 100, may be displayed on the display. Then, it is possible to confirm the information display screen 100 and the like even in the radiography room 25. A guide or the like of positioning for the subject H may be displayed.

Various screens, such as the information display screen 100, may be transmitted from the console 14 to a portable terminal, such as a tablet terminal, carried with the operator OP, for example, in a format of screen data for web distribution created by a markup language, such as an extensible markup language (XML). In this case, the portable terminal reproduces various screens that are displayed on a web browser based on screen data, and displays the screens on the display. Instead of the XML, other data description languages, such as Javascript (Registered Trademark) Object Notation (JSON), may be used.

Various modifications may be made to the hardware configuration of the computer that configures the console 14. For example, the console 14 may be configured with a plurality of computers separated as hardware for the purpose of improving processing capacity and reliability. For example, the functions of the first acquisition unit 75 and the extraction unit 76, and the functions of the derivation unit 77, the calculation unit 78, and the display control unit 79 may be assigned to two computers in a distributed manner. In this case, the console 14 is configured with two computers.

In this way, the hardware configuration of the computer of the console 14 may be appropriately changed depending on necessary performance, such as processing capacity, safety, and reliability. As well as hardware, an application program, such as the operation program 70, may be duplicated or may be stored in a plurality of storages in a distributed manner for the purpose of securing safety and reliability.

In the respective embodiments described above, for example, as a hardware structure of processing units that execute various kinds of processing, such as the first acquisition unit 75, the extraction unit 76, the derivation unit 77, the calculation unit 78, the display control unit 79, the first determination unit 130, the second acquisition unit 140, the second determination unit 141, and the reception unit 160, various processors described below can be used. Various processors include a programmable logic device (PLD) that is a processor capable of changing a circuit configuration after manufacturing, such as a field programmable gate array (FPGA), a dedicated electric circuit that is a processor having a circuit configuration dedicatedly designed for executing specific processing, such as an application specific integrated circuit (ASIC), and the like, in addition to the CPU 57 that is a general-purpose processor configured to execute software (operation program 70) to function as various processing units, as described above.

One processing unit may be configured with one of various processors or may be configured with a combination of two or more processors (for example, a combination of a plurality of ASICs and/or a combination of an ASIC and an FPGA) of the same type or different types. A plurality of processing units may be configured with one processor.

As an example where a plurality of processing units are configured with one processor, first, as represented by a computer, such as a client or a server, there is a form in which one processor is configured with a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, as the hardware structure of various processors, more specifically, an electric circuit (circuitry), in which circuit elements, such as semiconductor elements, are combined, can be used.

The technique of the present disclosure can also be appropriately combined with various embodiments and/or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner. The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. A radiography system comprising:
   a radiation source that irradiates a subject with radiation;
   a camera that is provided in the radiation source and images visible light reflected from the subject irradiated with light having uniform brightness to output an optical image; and
   a processor,
   wherein the processor is configured to:
   acquire the optical image, derive spinal column shape information representing a shape of a spinal column of the subject based on the optical image, extract a feature point of the subject from the optical image, extract derivation reference information for deriving the spinal column shape information from the feature point, derive a polynomial representing the shape of the spinal column as the spinal column shape information based on the derivation reference information, display, on a display, a spinal column shape derivation button that is selected to derive the spinal column shape information, and prior to the derivation of the spinal column shape information based on the optical image:

acquire information regarding a body height of the subject, extract right and left shoulder joint points and right and left hip joint points of the subject, as the feature point, determine whether or not the derivation of the spinal column shape information based on the optical image is needed, based on the body height of the subject and a length of a line that connects a middle point of a line connecting the right and left shoulder joint points and a middle point of a line connecting the right and left hip joint points, and disable the displayed spinal column shape derivation button upon determining that the derivation of the spinal column shape information is not needed.

2. The radiography system according to claim 1, wherein the processor is configured to calculate a Cobb angle indicating a degree of curvature of the spinal column from the polynomial.

3. The radiography system according to claim 2, wherein the processor is configured to perform control for displaying the Cobb angle on a display.

4. The radiography system according to claim 2, wherein the processor is configured to determine whether or not a secondary medical examination of scoliosis by radiography is needed for the subject, based on the Cobb angle, and perform control for displaying a determination result on a display.

5. The radiography system according to claim 1, wherein the processor is configured to extract right and left shoulder joint points, right and left hip joint points, points indicating a maximum width of right and left armpits of an upper body, and points indicating a minimum width of the right and left armpits of the upper body of the subject, as the feature point, and extract position coordinates of a middle point of a line connecting the right and left shoulder joint points, position coordinates of a middle point of a line connecting the right and left hip joint points, position coordinates of a middle point of a line connecting the points indicating the maximum width, and position coordinates of a middle point of a line connecting the points indicating the minimum width, as the derivation reference information.

6. The radiography system according to claim 1, wherein the processor is configured to extract right and left shoulder joint points and right and left hip joint points of the subject, as the feature point, and extract position coordinates of a middle point of a line connecting the right and left shoulder joint points, position coordinates of a middle point of a line connecting the right and left hip joint points, an inclination of the line connecting the right and left shoulder joint points, and an inclination of the line connecting the right and left hip joint points, as the derivation reference information.

7. The radiography system according to claim 1, wherein the processor is configured to perform control for displaying a past optical image acquired in a past on a display to be superimposed on a current optical image at the time of imaging preparation before the derivation of the spinal column shape information in a case of performing again the derivation of the spinal column shape information on the subject subjected to the derivation of the spinal column shape information based on the optical image in the past.

8. The radiography system according to claim 1, wherein the radiation source is a ceiling suspension type.

9. A method for operating a radiography system including a radiation source that irradiates a subject with radiation, the method comprising:

acquiring an optical image output from a camera that is provided in the radiation source and images the subject irradiated with light having uniform brightness;

deriving spinal column shape information representing a shape of a spinal column of the subject based on the optical image;

extracting a feature point of the subject from the optical image;

extracting derivation reference information for deriving the spinal column shape information from the feature point;

deriving a polynomial representing the shape of the spinal column as the spinal column shape information based on the derivation reference information;

displaying, on a display, a spinal column shape derivation button that is selected to derive the spinal column shape information; and prior to the derivation of the spinal column shape information based on the optical image:

acquiring information regarding a body height of the subject, extracting right and left shoulder joint points and right and left hip joint points of the subject, as the feature point, determining whether or not the derivation of the spinal column shape information based on the optical image is needed, based on the body height of the subject and a length of a line that connects a middle point of a line connecting the right and left shoulder joint points and a middle point of a line connecting the right and left hip joint points, and disabling the displayed spinal column shape derivation button upon determining that the derivation of the spinal column shape information is not needed.

10. A non-transitory computer-readable storage medium storing an operation program for a radiography system including a radiation source that irradiates a subject with radiation, the operation program causing a computer to execute a process, the process comprising:

acquiring an optical image output from a camera that is provided in the radiation source and images the subject irradiated with light having uniform brightness;

deriving spinal column shape information representing a shape of a spinal column of the subject based on the optical image;

extracting a feature point of the subject from the optical image;
extracting derivation reference information for deriving the spinal column shape information from the feature point;
deriving a polynomial representing the shape of the spinal column as the spinal column shape information based on the derivation reference information;
displaying, on a display, a spinal column shape derivation button that is selected to derive the spinal column shape information; and
prior to the derivation of the spinal column shape information based on the optical image:
  acquiring information regarding a body height of the subject,
  extracting right and left shoulder joint points and right and left hip joint points of the subject, as the feature point,
  determining whether or not the derivation of the spinal column shape information based on the optical image is needed, based on the body height of the subject and a length of a line that connects a middle point of a line connecting the right and left shoulder joint points and a middle point of a line connecting the right and left hip joint points, and
  disabling the displayed spinal column shape derivation button upon determining that the derivation of the spinal column shape information is not needed.

* * * * *